(12) United States Patent
Daniels

(10) Patent No.: US 12,295,621 B2
(45) Date of Patent: *May 13, 2025

(54) BOTTOM LOADED PEDICLE SCREW

(71) Applicant: OrthoPediatrics Corp., Warsaw, IN (US)

(72) Inventor: David W. Daniels, Winona Lake, IN (US)

(73) Assignee: OrthoPediatrics Corp., Warsaw, IN (US)

(*) Notice: Subject to any disclaimer, the term of this patent is extended or adjusted under 35 U.S.C. 154(b) by 377 days.

This patent is subject to a terminal disclaimer.

(21) Appl. No.: 17/843,034

(22) Filed: Jun. 17, 2022

(65) Prior Publication Data

US 2022/0323115 A1 Oct. 13, 2022

Related U.S. Application Data

(60) Continuation of application No. 16/382,543, filed on Apr. 12, 2019, now Pat. No. 11,389,206, which is a continuation of application No. 15/630,703, filed on Jun. 22, 2017, now Pat. No. 10,299,836, which is a division of application No. 15/219,677, filed on Jul. 26, 2016, now Pat. No. 9,820,782, which is a (Continued)

(51) Int. Cl.
*A61B 17/70* (2006.01)

(52) U.S. Cl.
CPC ...... *A61B 17/7037* (2013.01); *A61B 17/7032* (2013.01); *A61B 17/7035* (2013.01)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS

| 6,716,214 B1 | 4/2004 | Jackson |
| 7,322,981 B2 | 1/2008 | Jackson |
| 7,377,923 B2 | 5/2008 | Purcell et al. |

(Continued)

FOREIGN PATENT DOCUMENTS

WO 2015192057 A1 12/2015

OTHER PUBLICATIONS

International Search Report and Written Opinion received for International Application No. PCT/US2015/035629, mailed Sep. 15, 2015, 9 pages.

*Primary Examiner* — Ellen C Hammond
(74) *Attorney, Agent, or Firm* — Frost Brown Todd LLP

(57) ABSTRACT

A pedicle screw includes a tulip head, a rod seat, a screw shank, and a retainer collar. The tulip head has an upper opening disposed in a top end of the tulip head and a lower opening disposed in a bottom end of the tulip head opposite the upper opening. The upper and lower openings form a single cavity extending through the tulip head from a top end to the bottom end. The rod seat is disposed within the cavity of the tulip head. Retention ledges of the rod seat engage opposing arms of the tulip head. The screw shank has a thread disposed along a length of the screw shank and a connector positioned at an upper end. The retainer collar has a pass through aperture, an expansion slit, and is disposed about the connector of the screw shank. Other embodiments are described and claimed.

20 Claims, 26 Drawing Sheets

Related U.S. Application Data continuation of application No. PCT/US2015/035629, filed on Jun. 12, 2015.

(60) Provisional application No. 62/127,595, filed on Mar. 3, 2015, provisional application No. 62/011,865, filed on Jun. 13, 2014.

(56) References Cited

U.S. PATENT DOCUMENTS

| | | |
|---|---|---|
| 7,410,043 B2 | 8/2008 | Aulanko et al. |
| 7,722,652 B2 | 5/2010 | Justis et al. |
| 7,776,067 B2 | 8/2010 | Jackson |
| 7,875,065 B2 | 1/2011 | Jackson |
| 8,021,397 B2 | 9/2011 | Farris et al. |
| 8,137,386 B2 | 3/2012 | Jackson |
| 8,241,333 B2 | 8/2012 | Jackson |
| 8,267,969 B2 | 9/2012 | Altarac et al. |
| 8,277,490 B2 | 10/2012 | Freeman et al. |
| 8,298,265 B2 | 10/2012 | Purcell et al. |
| 8,353,932 B2 | 1/2013 | Jackson |
| 8,449,578 B2 | 5/2013 | Keiser et al. |
| 8,475,501 B2 | 7/2013 | Jackson |
| 8,540,753 B2 | 9/2013 | Jackson |
| 8,602,355 B2 | 12/2013 | McBroom |
| 8,696,711 B2 | 4/2014 | Jackson |
| 8,814,911 B2 | 8/2014 | Jackson |
| 8,840,652 B2 | 9/2014 | Jackson |
| 8,979,898 B2 | 3/2015 | Ark et al. |
| 8,998,959 B2 | 4/2015 | Jackson et al. |
| 9,308,027 B2 | 4/2016 | Jackson |
| 9,320,545 B2 | 4/2016 | Jackson |
| 9,451,993 B2 | 9/2016 | Jackson et al. |
| 9,456,853 B2 | 10/2016 | Jackson |
| 9,480,517 B2 | 11/2016 | Jackson et al. |
| 9,504,496 B2 | 11/2016 | Jackson et al. |
| 9,522,021 B2 | 12/2016 | Jackson et al. |
| 9,662,143 B2 | 5/2017 | Jackson |
| 9,700,354 B2 | 7/2017 | Jackson |
| 9,788,866 B2 | 10/2017 | Jackson |
| 9,808,292 B2 | 11/2017 | Jackson |
| 9,820,782 B2 | 11/2017 | Daniels |
| 9,980,753 B2 | 5/2018 | Jackson et al. |
| 10,039,571 B2 | 8/2018 | Jackson |
| 10,039,577 B2 | 8/2018 | Jackson |
| 10,058,354 B2 | 8/2018 | Jackson et al. |
| 10,085,774 B2 | 10/2018 | Jackson |
| 10,188,432 B2 | 1/2019 | Jackson et al. |
| 10,278,738 B2 | 5/2019 | Jackson et al. |
| 10,278,739 B2 | 5/2019 | Jackson |
| 10,278,740 B2 | 5/2019 | Jackson |
| 10,299,835 B2 | 5/2019 | Jackson |
| 10,299,836 B2 | 5/2019 | Daniels |
| 10,335,200 B2 | 7/2019 | Jackson |
| 10,349,983 B2 | 7/2019 | Purcell et al. |
| 10,363,070 B2 | 7/2019 | Jackson et al. |
| 10,398,474 B2 | 9/2019 | Jackson |
| 10,524,840 B2 | 1/2020 | Purcell et al. |
| 10,537,365 B2 | 1/2020 | Purcell et al. |
| 10,537,366 B2 | 1/2020 | Purcell et al. |
| 10,543,020 B2 | 1/2020 | Jackson |
| 10,561,444 B2 | 2/2020 | Jackson |
| 10,561,445 B2 | 2/2020 | Jackson |
| 10,588,667 B2 | 3/2020 | Purcell et al. |
| 10,595,905 B2 | 3/2020 | Purcell et al. |
| 10,595,906 B2 | 3/2020 | Purcell et al. |
| 10,617,448 B2 | 4/2020 | Purcell et al. |
| 10,695,101 B2 | 6/2020 | Jackson |
| 10,702,309 B2 | 7/2020 | Jackson |
| 10,722,273 B2 | 7/2020 | Jackson |
| 10,751,093 B2 | 8/2020 | Purcell et al. |
| 10,765,455 B2 | 9/2020 | Jackson et al. |
| 10,792,074 B2 | 10/2020 | Jackson |
| 10,799,272 B2 | 10/2020 | Jackson |
| 10,813,671 B2 | 10/2020 | Jackson et al. |
| 10,813,672 B2 | 10/2020 | Jackson et al. |
| 10,856,911 B2 | 12/2020 | Jackson et al. |
| 10,874,437 B2 | 12/2020 | Jackson |
| 10,939,940 B2 | 3/2021 | Jackson et al. |
| 10,945,768 B2 | 3/2021 | Jackson et al. |
| 10,952,777 B2 | 3/2021 | Jackson |
| 11,000,314 B2 | 5/2021 | Jackson |
| 11,013,537 B2 | 5/2021 | Jackson |
| 11,039,861 B2 | 6/2021 | Purcell et al. |
| 11,045,229 B2 | 6/2021 | Jackson |
| 11,051,856 B2 | 6/2021 | Jackson |
| 11,076,889 B2 | 8/2021 | Jackson |
| 11,134,993 B2 | 10/2021 | Jackson |
| 11,147,597 B2 | 10/2021 | Jackson |
| 11,197,696 B2 | 12/2021 | Jackson |
| 11,219,471 B2 | 1/2022 | Jackson et al. |
| 11,219,474 B2 | 1/2022 | Jackson |
| 11,234,745 B2 | 2/2022 | Jackson |
| 11,246,627 B2 | 2/2022 | Jackson |
| 11,389,206 B2 | 7/2022 | Daniels |
| 11,389,207 B2 | 7/2022 | Purcell et al. |
| 11,419,636 B2 | 8/2022 | Jackson et al. |
| 11,419,638 B2 | 8/2022 | Jackson |
| 11,426,207 B2 | 8/2022 | Jackson |
| 11,471,195 B2 | 10/2022 | Jackson et al. |
| 11,583,319 B2 | 2/2023 | Jackson |
| 11,596,449 B2 | 3/2023 | Jackson et al. |
| 11,684,396 B2 | 6/2023 | Jackson |
| 11,717,328 B2 | 8/2023 | Jackson |
| 11,730,526 B2 | 8/2023 | Jackson et al. |
| 11,737,789 B2 | 8/2023 | Jackson |
| 11,737,790 B2 | 8/2023 | Jackson |
| 11,751,915 B2 | 9/2023 | Jackson et al. |
| 11,751,916 B2 | 9/2023 | Jackson et al. |
| 11,751,917 B2 | 9/2023 | Jackson et al. |
| 11,779,374 B2 | 10/2023 | Jackson et al. |
| 11,819,248 B2 | 11/2023 | Purcell et al. |
| 11,819,249 B2 | 11/2023 | Jackson et al. |
| 11,911,075 B2 | 2/2024 | Jackson et al. |
| 11,918,256 B2 | 3/2024 | Jackson et al. |
| 11,925,392 B2 | 3/2024 | Jackson |
| 11,957,386 B2 | 4/2024 | Jackson |
| 11,998,247 B2 | 6/2024 | Jackson et al. |
| 12,042,185 B2 | 7/2024 | Jackson |
| 12,053,209 B2 | 8/2024 | Jackson et al. |
| 12,053,217 B2 | 8/2024 | Jackson et al. |
| 12,070,249 B2 | 8/2024 | Jackson et al. |
| 12,076,055 B2 | 9/2024 | Jackson et al. |
| 12,082,850 B2 | 9/2024 | Jackson |
| 12,082,854 B2 | 9/2024 | Jackson et al. |
| 12,096,964 B2 | 9/2024 | Jackson et al. |
| 12,102,357 B2 | 10/2024 | Jackson |
| 12,137,945 B2 | 11/2024 | Jackson et al. |
| 12,167,872 B2 | 12/2024 | Jackson et al. |
| 2003/0004512 A1 | 1/2003 | Farris et al. |
| 2003/0153911 A1 | 8/2003 | Shluzas |
| 2004/0097933 A1 | 5/2004 | Lourdel et al. |
| 2004/0116929 A1 | 6/2004 | Barker et al. |
| 2006/0100621 A1 | 5/2006 | Jackson |
| 2006/0100622 A1 | 5/2006 | Jackson |
| 2006/0149240 A1 | 7/2006 | Jackson |
| 2007/0118117 A1 | 5/2007 | Altarac et al. |
| 2008/0015579 A1 | 1/2008 | Whipple |
| 2008/0015597 A1 | 1/2008 | Whipple |
| 2012/0109218 A1 | 5/2012 | Farris |
| 2012/0310284 A1 | 12/2012 | Gerchow |
| 2013/0296951 A1* | 11/2013 | Jackson ............ A61B 17/7032 606/308 |
| 2016/0331413 A1 | 11/2016 | Daniels |
| 2017/0281242 A1 | 10/2017 | Daniels |
| 2019/0231397 A1 | 8/2019 | Daniels |
| 2022/0047306 A1 | 2/2022 | Jackson |
| 2022/0168018 A1 | 6/2022 | Jackson |
| 2023/0057541 A1 | 2/2023 | Jackson et al. |
| 2023/0270470 A1 | 8/2023 | Jackson et al. |
| 2023/0277223 A1 | 9/2023 | Jackson |
| 2023/0363799 A1 | 11/2023 | Jackson |
| 2023/0404629 A1 | 12/2023 | Jackson |
| 2024/0081872 A1 | 3/2024 | Jackson et al. |

(56) References Cited

U.S. PATENT DOCUMENTS

| | | |
|---|---|---|
| 2024/0122634 A1 | 4/2024 | Jackson |
| 2024/0197369 A1 | 6/2024 | Jackson et al. |
| 2024/0216020 A1 | 7/2024 | Jackson |
| 2024/0252212 A1 | 8/2024 | Jackson et al. |
| 2024/0252213 A1 | 8/2024 | Jackson |

* cited by examiner

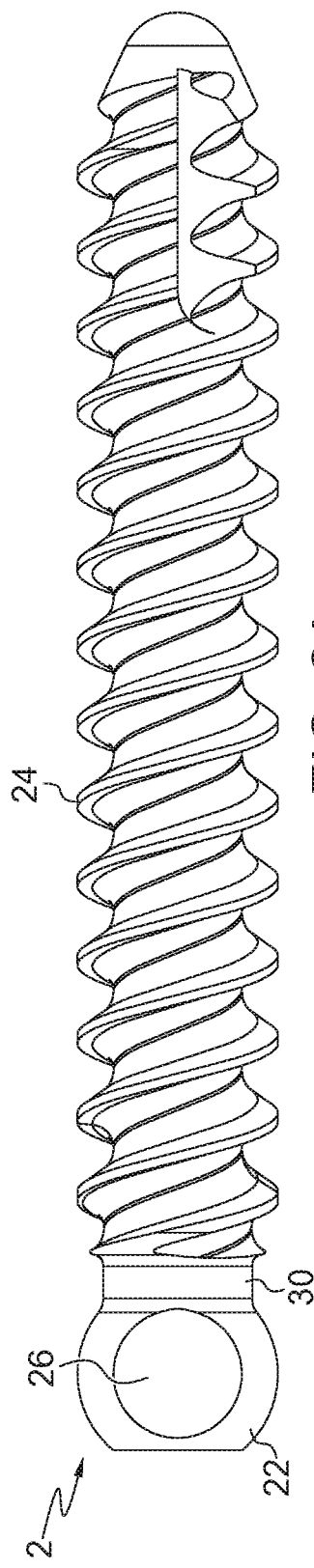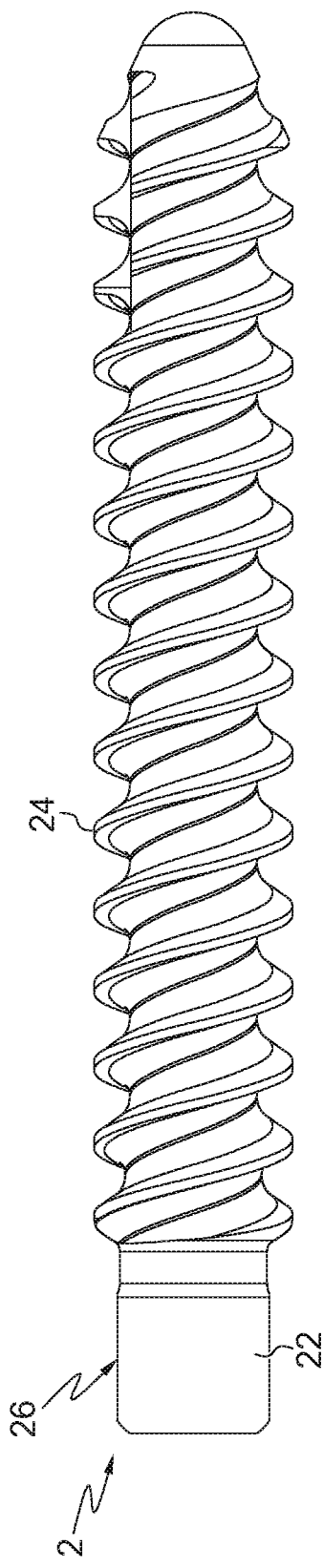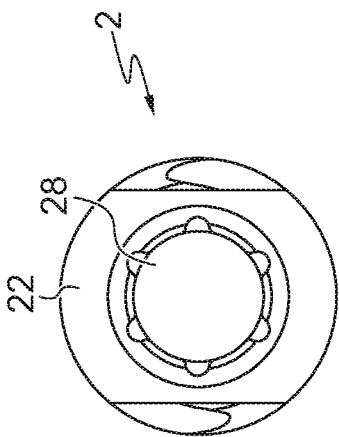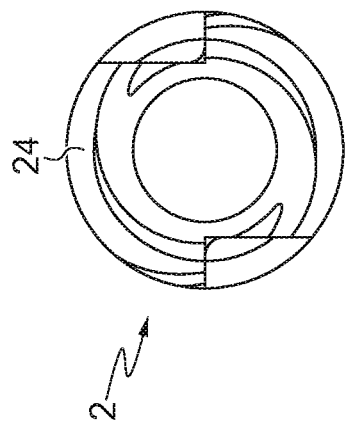

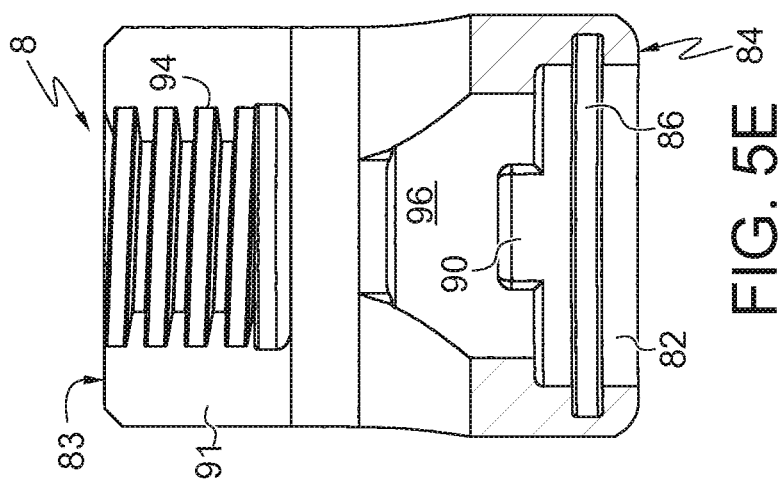
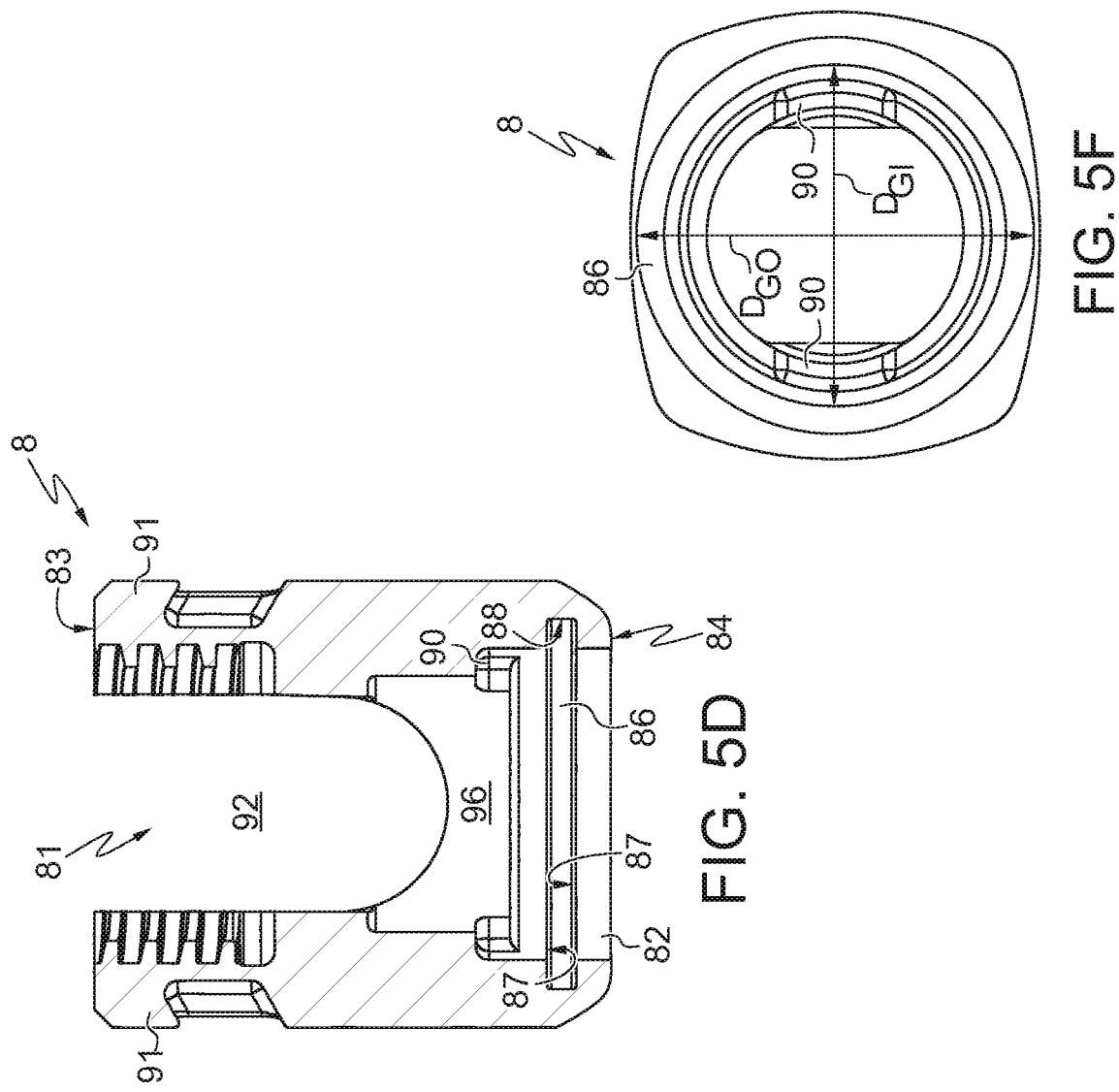

BOTTOM LOADED PEDICLE SCREW

CROSS REFERENCE TO RELATED APPLICATIONS

The present application is a continuation of U.S. application Ser. No. 16/382,543, filed on Apr. 12, 2019, which is a continuation of U.S. application Ser. No. 15/630,703, filed on Jun. 22, 2017 and now U.S. Pat. No. 10,299,836, which is a division of U.S. application Ser. No. 15/219,677, filed on Jul. 26, 2016 and now U.S. Pat. No. 9,820,782, which is a continuation of International Application No. PCT/US2015/035629, filed on Jun. 12, 2015, which claims the benefit of Provisional U.S. Application No. 62/127,595, filed on Mar. 3, 2015, and Provisional U.S. Application No. 62/011,865, filed on Jun. 13, 2014, each of which is hereby incorporated herein by reference in its entirety.

BRIEF DESCRIPTION OF THE DRAWINGS

The present disclosure may be more easily understood with reference to the figures, which are as follow:

FIG. 2A is a side elevational view of a screw shank of FIG. 1A;

FIG. 2B is a front view of the screw shank of FIG. 2A;

FIG. 2C is a bottom plan view of the screw shank of FIG. 2A;

FIG. 2D is a top plan view of the screw shank of FIG. 2A;

FIG. 5D is a cross sectional view of the tulip head of FIG. 5A;

FIG. 5E is a cross section view of the tulip head of FIG. 5A;

FIG. 5F is a cross section view of the tulip head of FIG. 5A, taken laterally across the tulip head of FIG. 5A along the retention groove;

DETAILED DESCRIPTION

The following text sets forth a broad description of numerous different embodiments. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Embodiments described herein generally relate to a pedicle screw for spinal surgical procedure such as the amelioration and/or correction of scoliosis or other conditions of the spine wherein the threaded screw shank is loaded into the head from the bottom. A pedicle screw is typically inserted into the area of the vertebrae bones that is between the upper and lower facet joints called the pars articularis or pedicle.

Figure 1A:
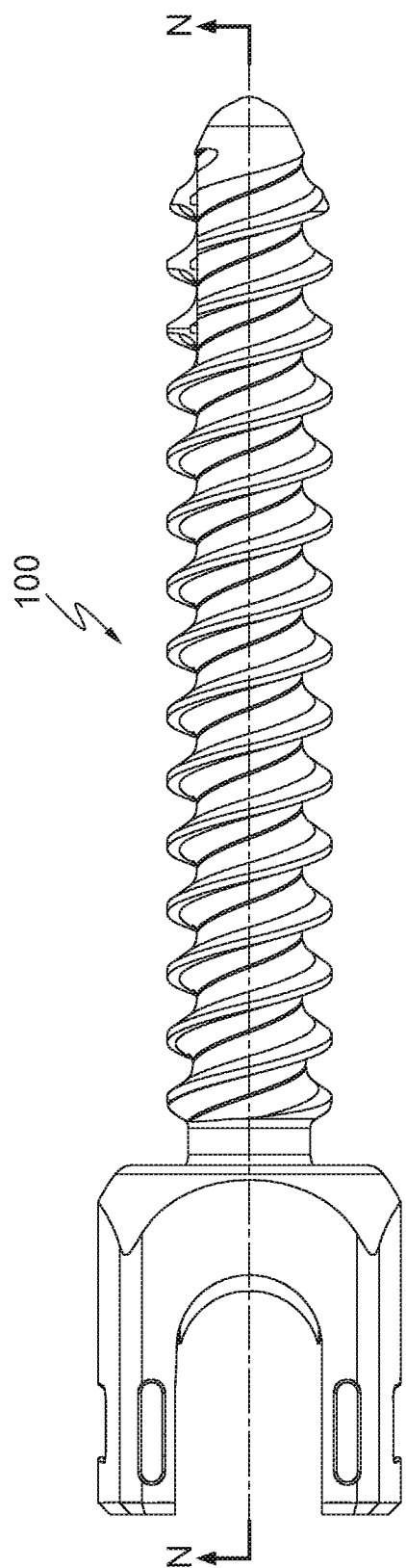
FIG. 1A is a side elevational view of an embodiment of a pedicle screw according to one or more embodiments.
Figure 1B:
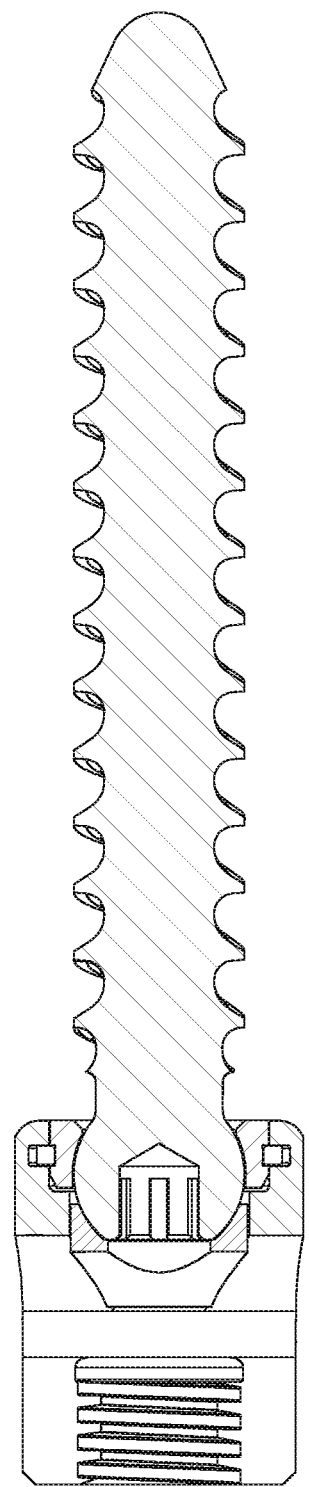
FIG. 1B is a cross sectional view of the pedicle screw of FIG. 1A, taken along N-N.

Referring to FIGS. 1A-1C and 9A-B, a pedicle screw 100 is shown. FIG. 1B is a longitudinal cross sectional view of pedicle screw 100 taken along section line, N-N. In the illustrative embodiment shown, pedicle screw 100 includes a screw shank 2, retainer collar 4, locking ring 6, tulip head 8, and rod seat 10. When assembled together, these components form pedicle screw 100. Each of the components set forth above will be individually described below herein and shown in separate figures. In addition, it will be shown and described below herein how each of the components of the pedicle screw 100 are interconnected and, once assembled, how the pedicle screw 100 works in operation.

Figure 13A:
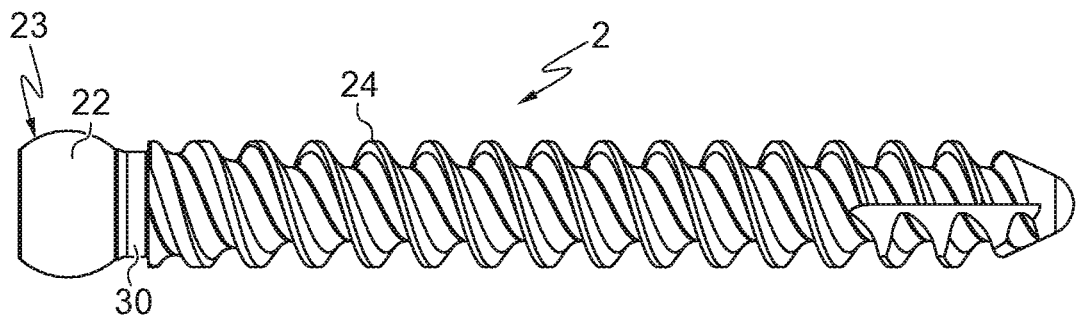
FIG. 13A is a side elevational view of the screw shank of FIG. 12.
Figure 13B:
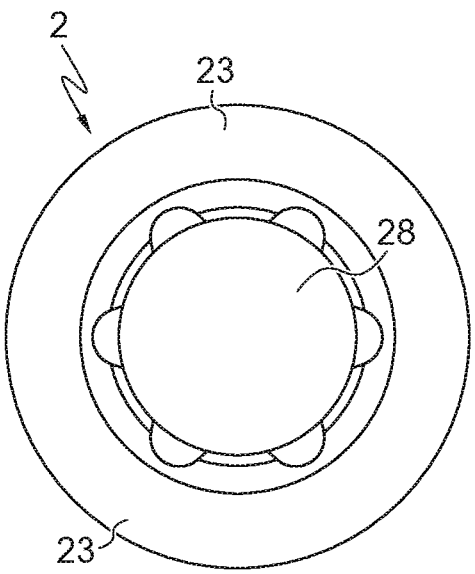
FIG. 13B is a top plan view of the screw shank of FIG. 13A.

Referring to FIGS. 2A-2D and 13A-13B, screw shank 2 of pedicle screw 100 is shown. Screw shank 2 comprises at least one helical thread 24 formed along the length thereof. It is important to note that the proportions of the bone screw depicted are for illustrative purposes only and variations in the length of the shank, diameter of the screw, thread pitch, thread length, number of thread leads, shank induced compression and the like may be varied without departing from the scope of the disclosure. As will be further described later in this specification, screw shanks of various widths and with various thread sizes are compatible with the same tulip head 8 reducing the manufacturing inventory. At the upper end of the screw shank 2 is a spherical connector 22 having a predetermined diameter. In an embodiment, the spherical connector 22 includes a spherical surface 23 spanning a full 360 degrees around the spherical connector 22. Such an arrangement is developed for a poly-axial pedicle screw capable of angulations between the screw shank 2 and the tulip head 8 along multiple axes and is shown in FIGS. 13A-13B, for example. In another embodiment the spherical connector 22 includes angulation guides 26 on opposed sides of the spherical connector 22 as illustrated in FIGS. 2A-2B. The angulation guides 26 are planar surfaces formed by removal of the segments of the spherical connector 22 formed by planes intersecting the spherical connector 22 on opposed sides circumferentially offset 180°. Such an arrangement is developed for a uni-axial pedicle screw capable of angulation between the screw shank 2 and the tulip head 8 along a single axis. A shank collar 30 connects the spherical connector 22 and the helical threaded portion. The shank collar 30 is a section of the screw shank 2 of reduced diameter which transitions between the spherical connector 22 and the threaded portion of the screw shank 2. The shank collar 30 provides clearance between the tulip head 8 and the helical thread 24. In an embodiment, the diameter of the shank collar 30 is approximately the same as the minor diameter of the helical thread 24. Further, a driver receptacle 28 is located along the upper end of the spherical connector 22 for use in installing the pedicle screw 100 by use of a driving tool. It should be noted that the driver receptacle 28 may be any shape, male or female, suitable for cooperation with a driving tool to rotate the pedicle screw 100 into its final position.

Figure 12:
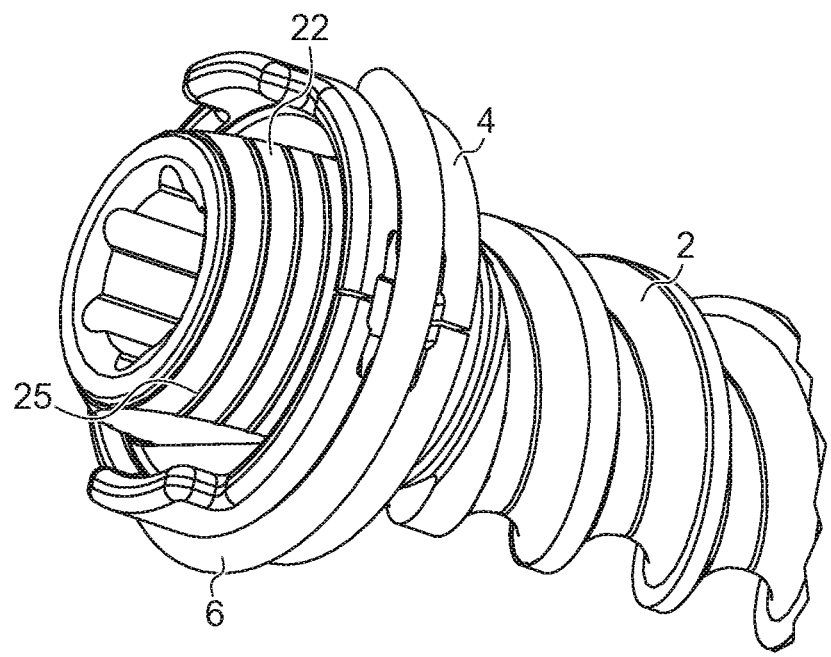
FIG. 12 is a partial isometric view of another embodiment of a screw shank of FIG. 1A.

The spherical connector 22 of the screw shank 2 has multiple geometries. In an embodiment, the spherical connector 22 is smooth without ridges or other surface perturbances as shown in FIGS. 2A and 2B for example. Specifically, the spherical portion of the spherical connector 22 maintains a spherical geometry within the bounds of normal machining or manufacturing variances. In another embodiment, the spherical connector 22 comprises surface perturbances 25 as shown in FIG. 12 for example. In various embodiments, the surface perturbances are ridges, grooves, or surface roughness. The perturbances may be formed in a vertical, horizontal, radial, crosshatched, circular, isotropic arrangement on the spherical connector 22 surface. The surface protuberances provide increased friction and/or adhesion between the screw shank 2, the retainer collar 4, and the rod seat 10.

Referring to FIGS. 3A-3E, 4A-4B, and 10A-10E, retainer collar 4 of pedicle screw 100 is shown. In various embodiments, the retainer collar 4 comprises two semicircular collar halves 4a/4b which combine to form a partial or full annular profile. In various other embodiments, the retainer collar 4 comprises a singular annular structure with a collar expansion split 54 disposed therein to allow expansion of the retainer collar 4. As shown, the retainer collar 4 has an outer diameter ($D_{CO}$) in its operational position.

In an embodiment, each segment of the retainer collar 4 includes an anti-rotation tab 32. The anti-rotation tab 32 projects from a top surface of the retainer collar 4 and is configured to mate with a corresponding anti-rotation socket 90 in the tulip head 8. In a uni-axial pedicle screw 100, prevention of rotation of the retainer collar 4 in turn prevents rotation of the screw shank 2 relative to tulip head 8. Rotation of screw shank 2 relative to tulip head 8 in a uni-axial screw is generally not desirable as the direction of pivot would also rotate. In an embodiment of a uni-axial pedicle screw 100, anti-rotation tabs 32 are omitted to allow angulation and manipulation of tulip head 8 after insertion of screw shank 2 into a patient's bone. In a poly-axial pedicle screw 100 rotation of the screw shank 2 relative to the tulip head 8 is not generally a concern so the anti-rotation tabs 32 may be omitted or retained.

Figure 4A:
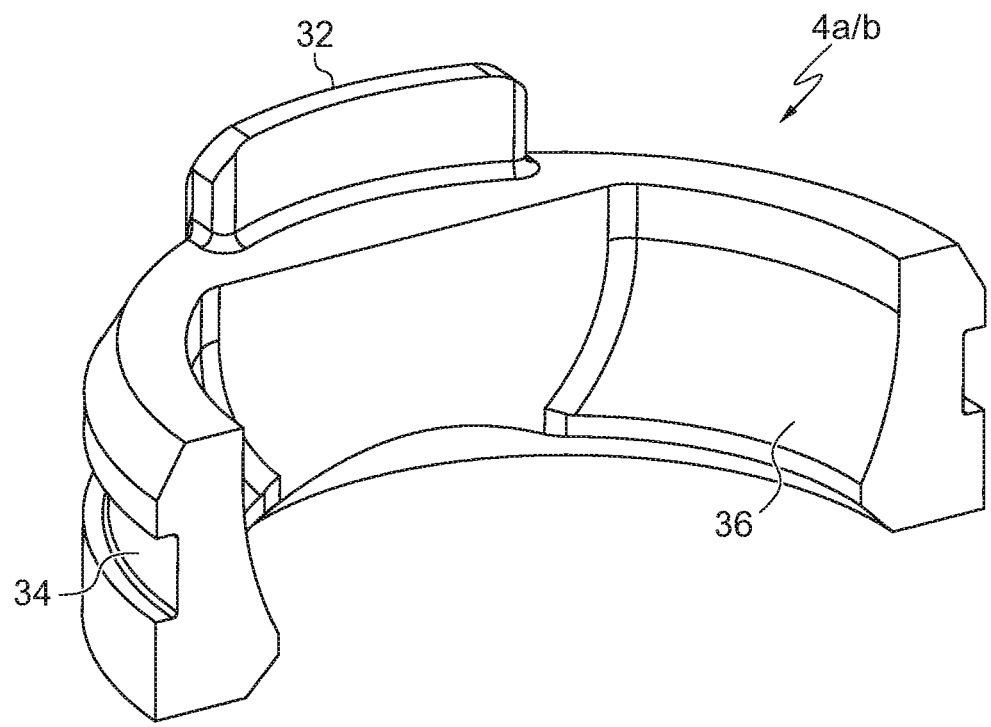
FIG. 4A is an isometric view of one half of the retainer collar of FIG. 3A.
Figure 4B:
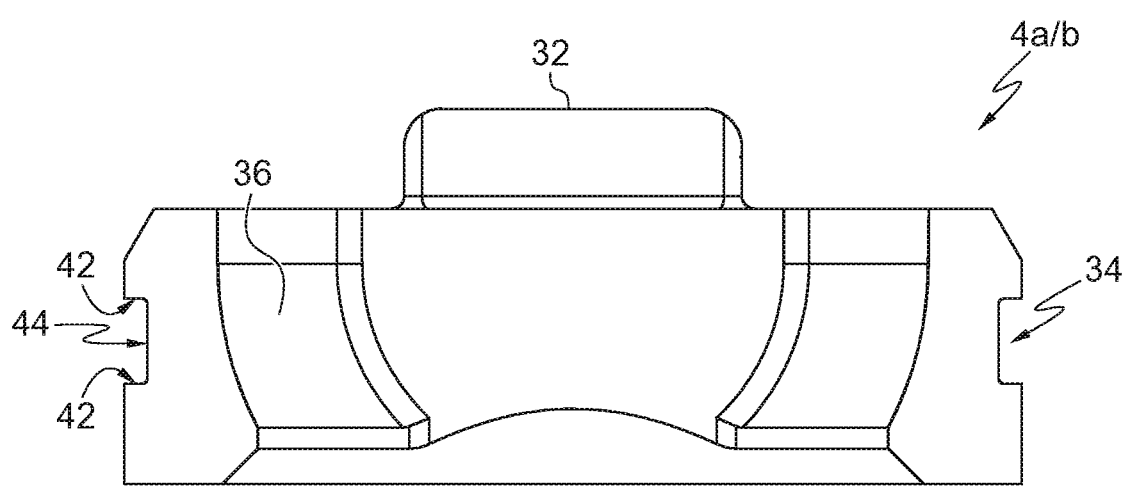
FIG. 4B is a ride side elevational view of the one halve of the retainer collar of FIG. 4A.

The retainer collar 4 comprises a locking ring groove 34. The locking ring groove 34 is disposed on the outer surface of the retainer collar 4 and forms a recessed channel. In an embodiment, the locking ring groove 34 has two side walls 42 and a bottom wall 44 as shown in FIGS. 1B and 4B, for example. In another embodiment, the locking ring groove 34 has a semicircular profile as shown in FIGS. 9B and 10A-10E, for example. The locking ring groove 34 is sized and configured to accept a locking ring 6.

Figure 3A:
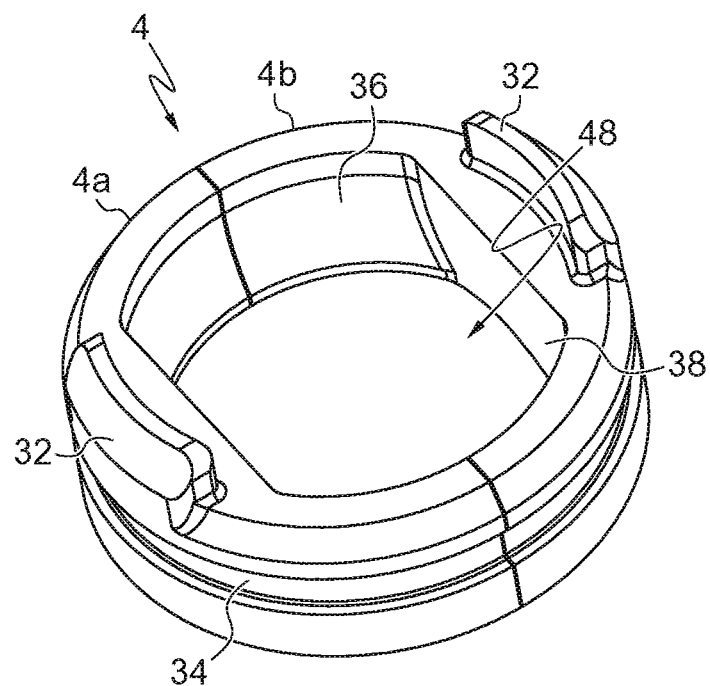
FIG. 3A is an isometric view of a retainer collar of FIG. 1A.
Figure 3B:
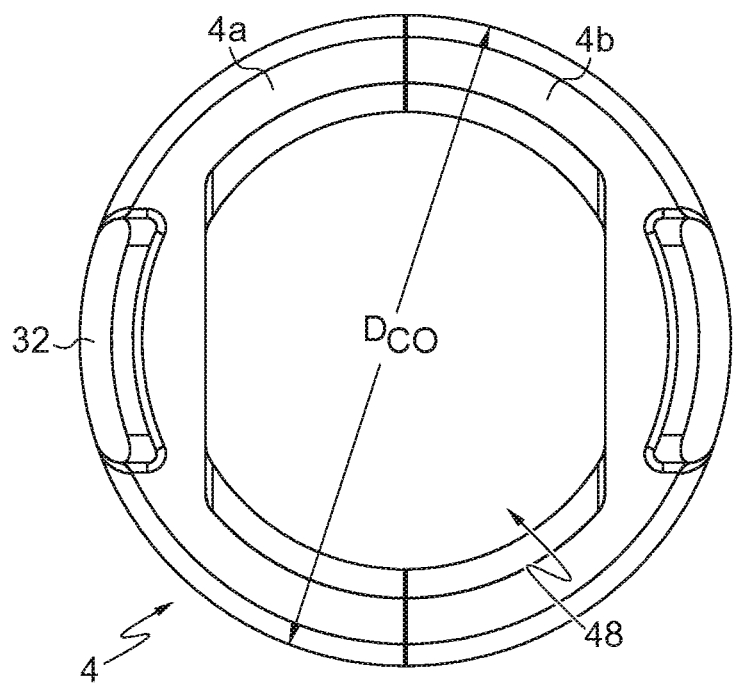
FIG. 3B is a top plan view of the retainer collar of FIG. 3A.
Figure 3C:
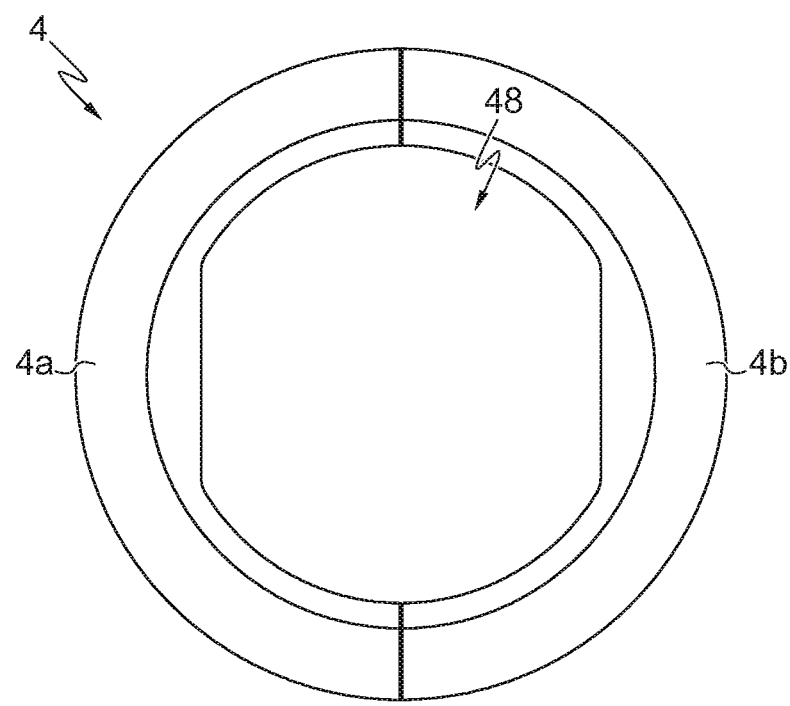
FIG. 3C is a bottom plan view of the retainer collar of FIG. 3A.
Figures 3D, 3E:
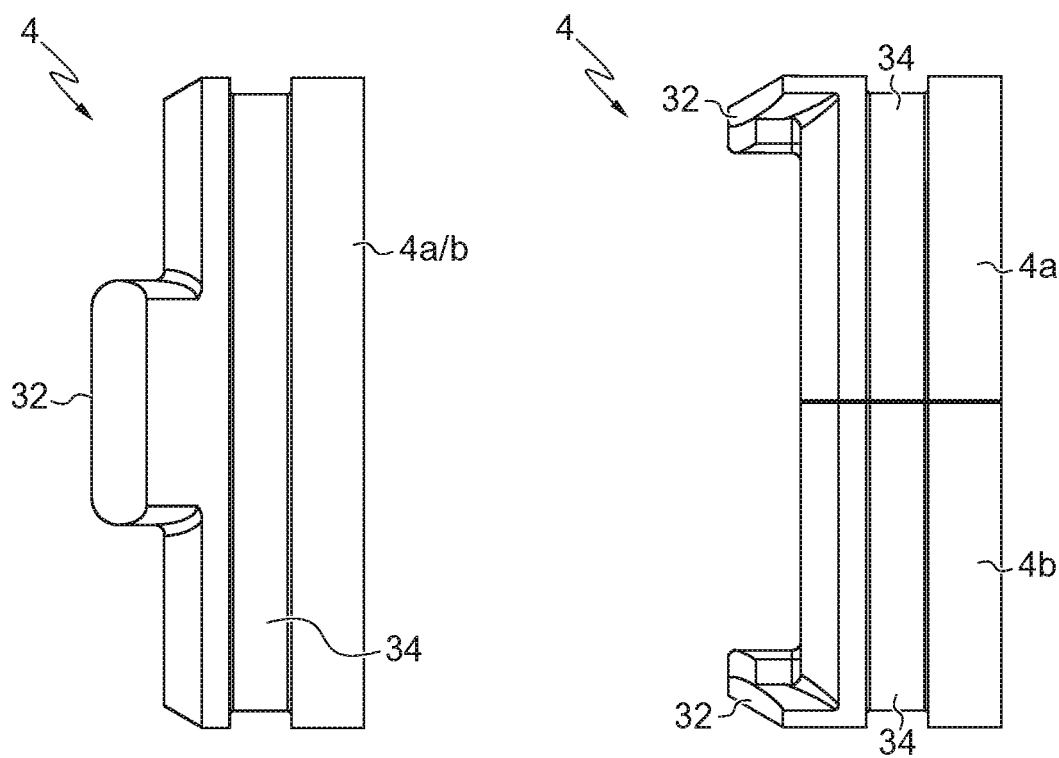
FIG. 3D is a right side elevational view of the retainer collar of FIG. 3A.
FIG. 3E is a front view of the retainer collar of FIG. 3A.
Figure 10A:
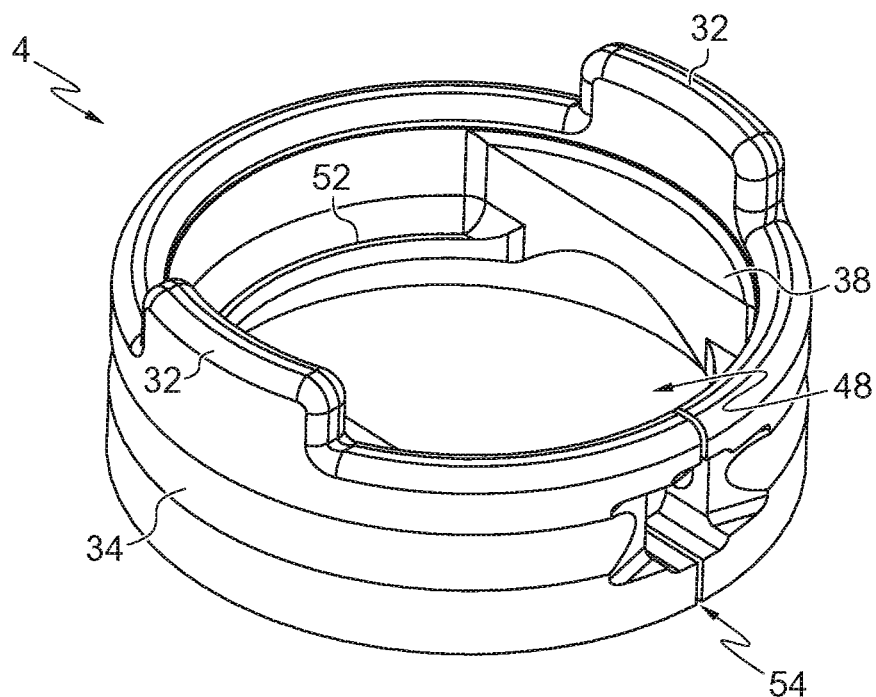
FIG. 10A is a isometric view of another embodiment of a retainer collar of FIG. 1A.
Figure 10B:
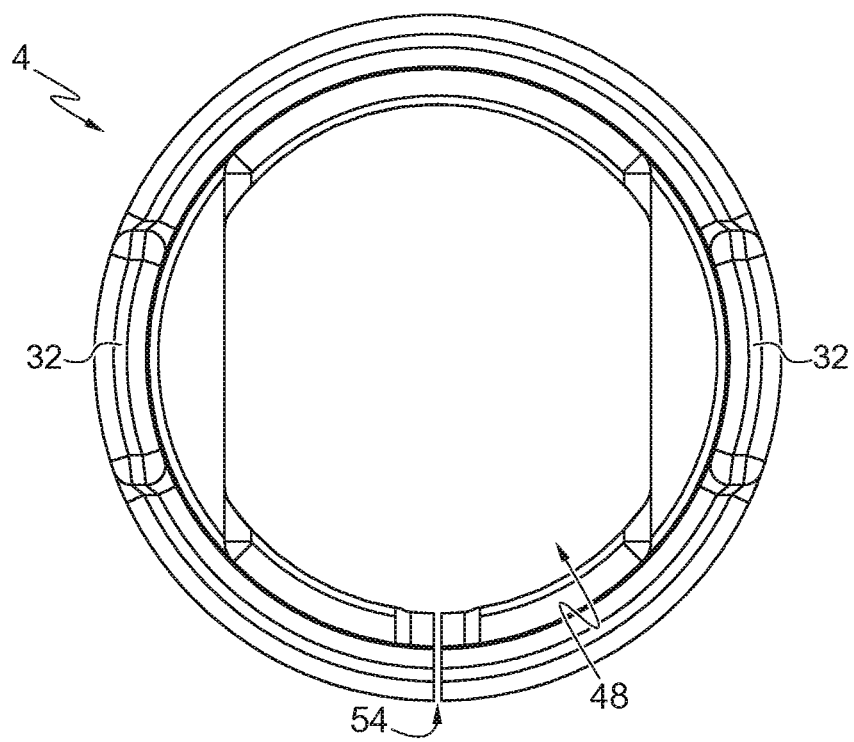
FIG. 10B is top plan view of the retainer collar of FIG. 10A.
Figure 10C:
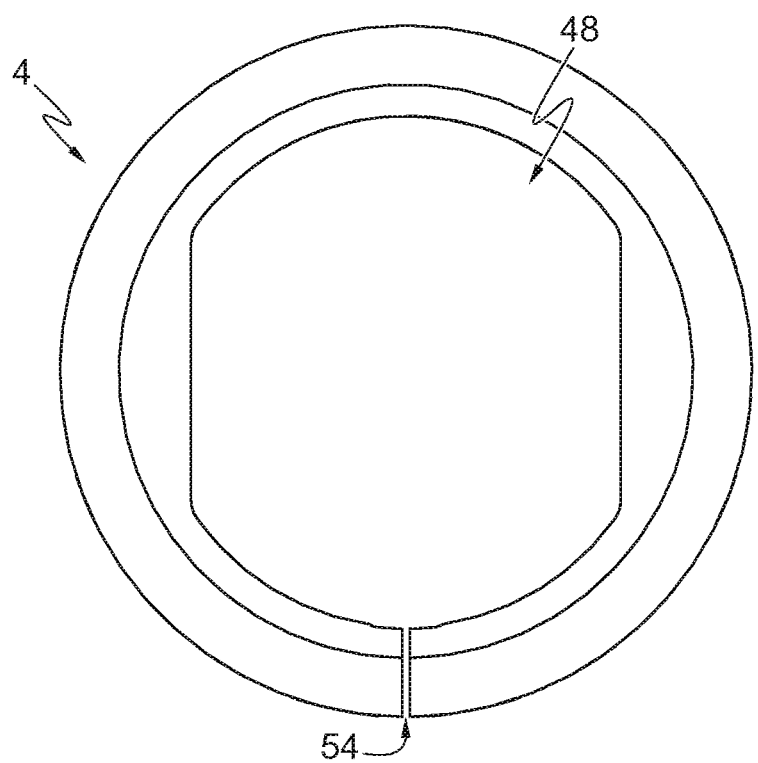
FIG. 10C is a bottom plan view of the retainer collar of FIG. 10A.
Figures 10D, 10E:
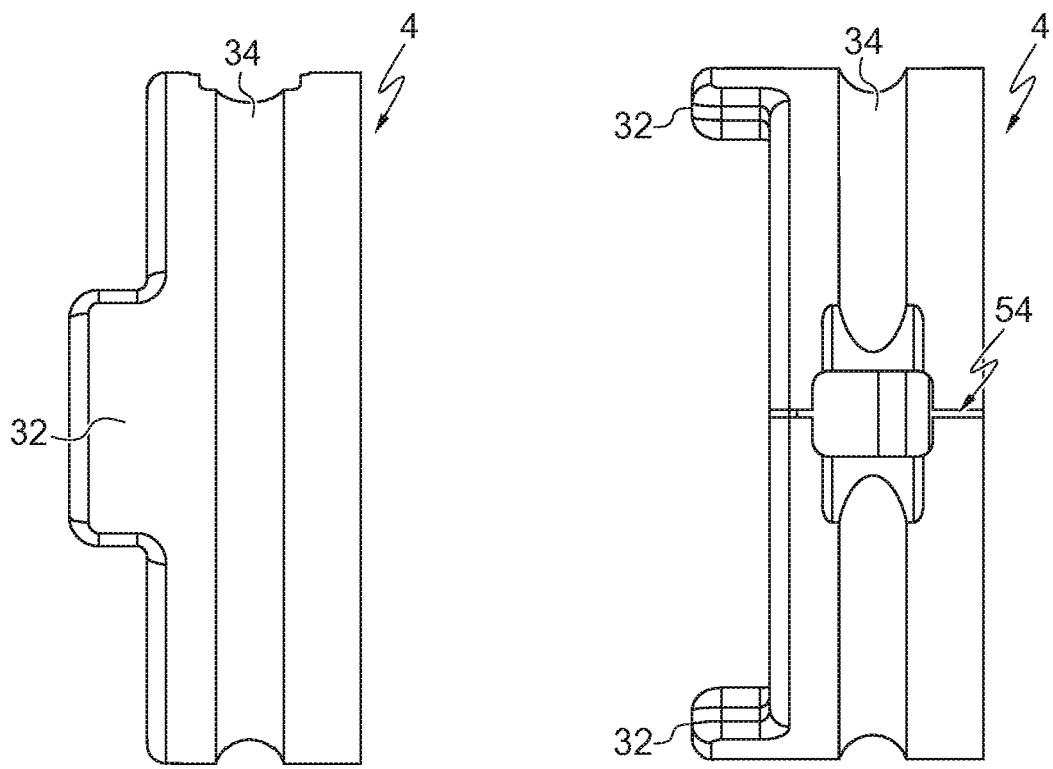
FIG. 10D is a right side elevational view of the retainer collar of FIG. 10A.
FIG. 10E is front view of the retainer collar of FIG. 10A.
Figure 11:
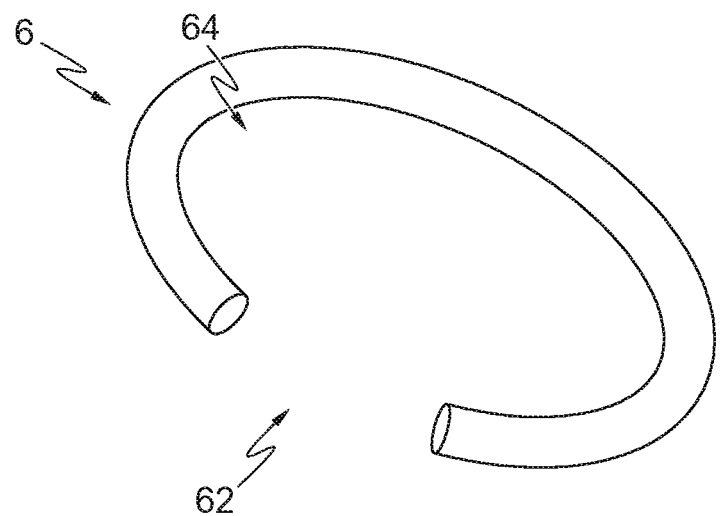
FIG. 11 is an isometric view of a locking ring of FIG. 1A.
Figure 13C:
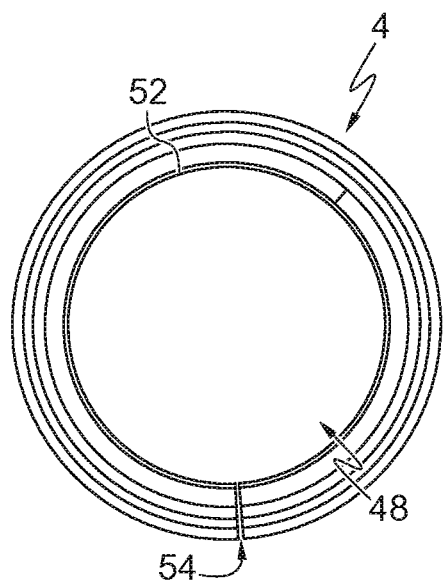
FIG. 13C is a bottom plan view of another embodiment of a retainer collar of FIG. 10A.
Figure 13D:
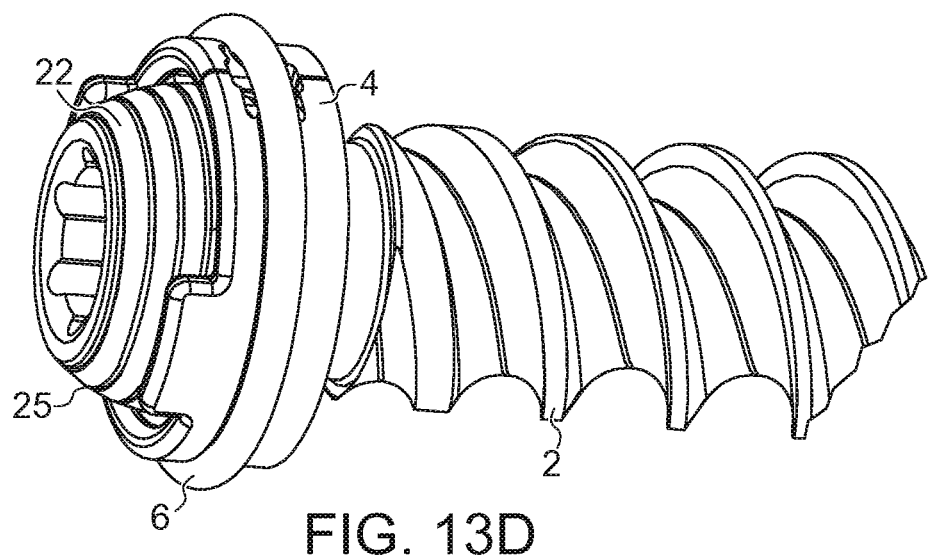
FIG. 13D is an isometric view of the screw shank of FIG. 13A with the retainer collar of FIG. 13C coupled thereon.
Figure 14:
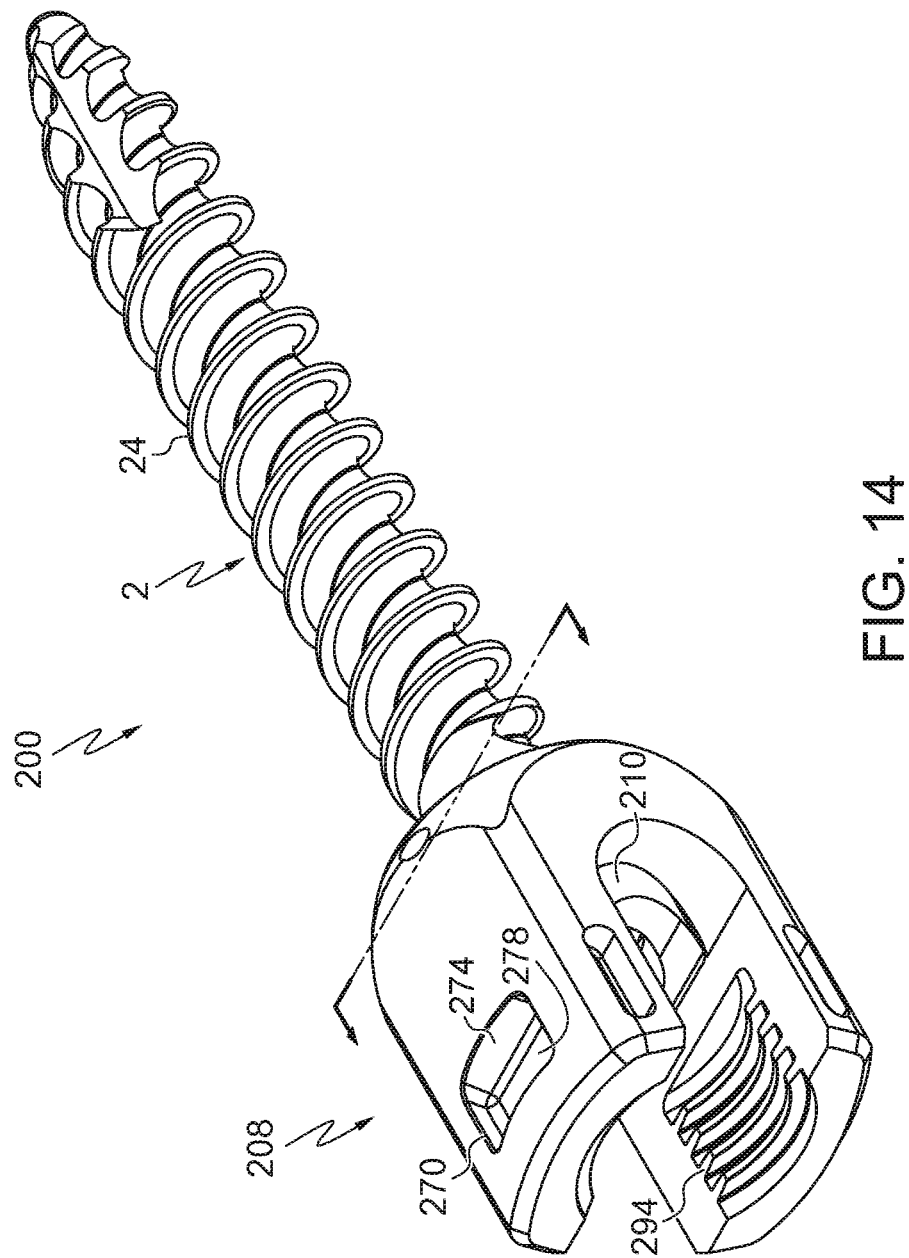
FIG. 14 is an isometric view of another embodiment of a pedicle screw according to one or more embodiment.

In an embodiment, the interior surface of the retainer collar 4 includes a spherical connector mating surface 36 sized and configured to interface and mate with the spherical connector 22 of the screw shank 2. In an embodiment, specifically a poly-axial pedicle screw 100, the spherical connector mating surface 36 comprises a curved surface matching the curved profile of the spherical connector 22 and the curved profile extends the full 360° profile of the interior surface of the retainer collar 4 as shown in FIG. 13C. In another embodiment, specifically a uni-axial pedicle screw 100, the spherical connector mating surface 36 comprises a curved surface matching the curved profile of the spherical connector 22 as well as flat planar surfaces 38 matching the angulation guides 26 of the spherical connector 22 as shown in FIGS. 3A and 10A. The arrangement of the curved profile and planar surfaces match the arrangement of the spherical portions and the angulation guides 26 of the spherical connector 22.

In a further embodiment, the retainer collar 4 comprises a shepherical connector mating edge 52 as shown in FIG. 10A. The spherical connector mating edge 52 interfaces with the spherical connector 22 of the screw shank 2. In an embodiment, the spherical connector mating edge 52 comprises a sharp edge which cuts or depresses into the spherical connector 22 upon insertion and tightening of a connector rod into the pedicle screw 100.

The retainer collar 4 retains the spherical connector 22 of the screw shank 2. A screw shank pass-through aperture 48 is formed in retainer collar 4. The screw shank pass-through aperture 48 is sized to fit around the shank collar 30 of the screw shank 2 but prevent passage of the spherical connector 22. In an embodiment, the screw shank pass-through aperture 48 is formed by the two semicircular collar halves 4a/4b when combined together, with each of the two semicircular collar halves 4a/4b forming approximately half of the screw shank pass-through aperture 48. In a further embodiment, wherein retainer collar 4 is a single piece, screw shank pass-through aperture 48 is naturally formed by the annular configuration of the retainer collar 4.

Figure 5A:
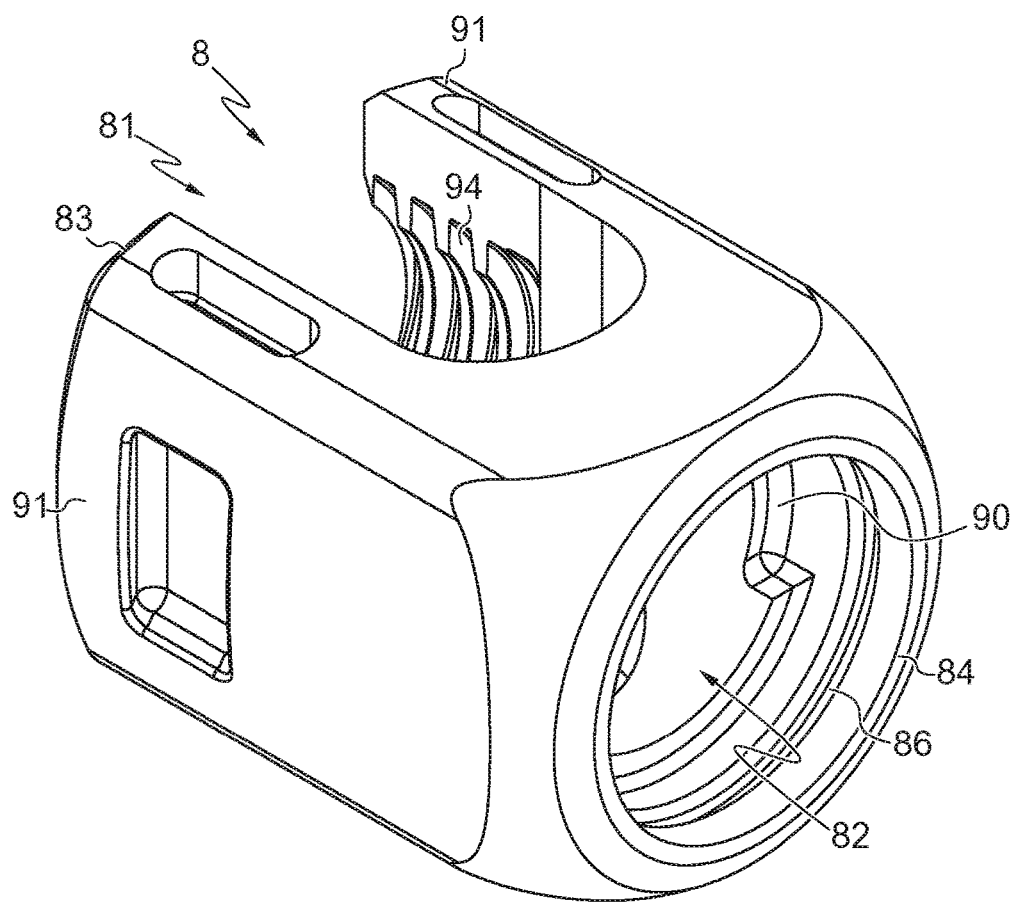
FIG. 5A is an isometric view of a tulip head of FIG. 1A.
Figure 5B:
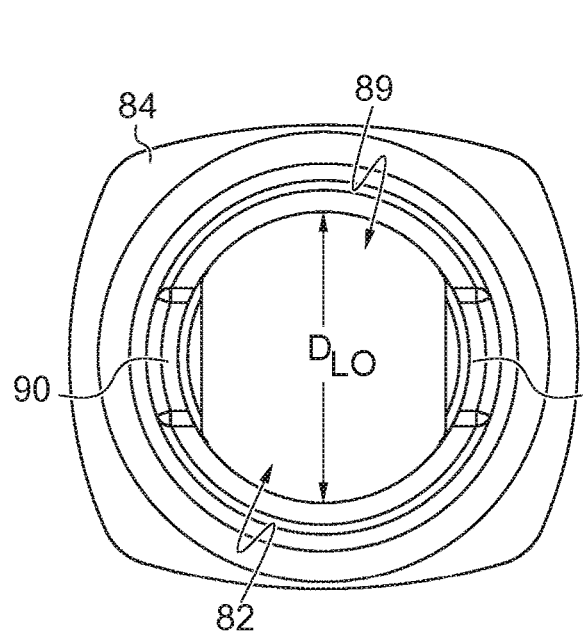
FIG. 5B is a bottom plan view of the tulip head of FIG. 5A.
Figure 5C:
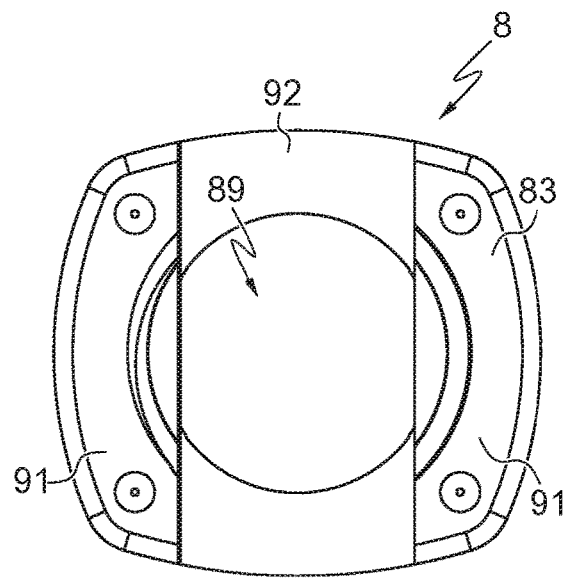
FIG. 5C is a top plan view of the tulip head of FIG. 5A.
Figure 6A:
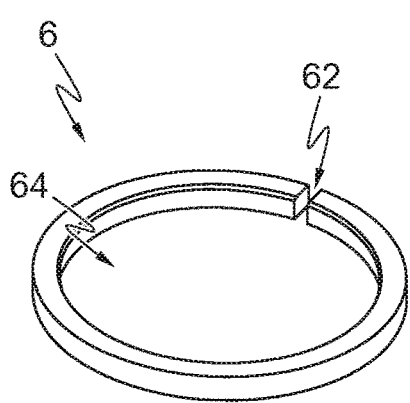
FIG. 6A is an isometric view of a locking ring of FIG. 1A.
Figure 6B:
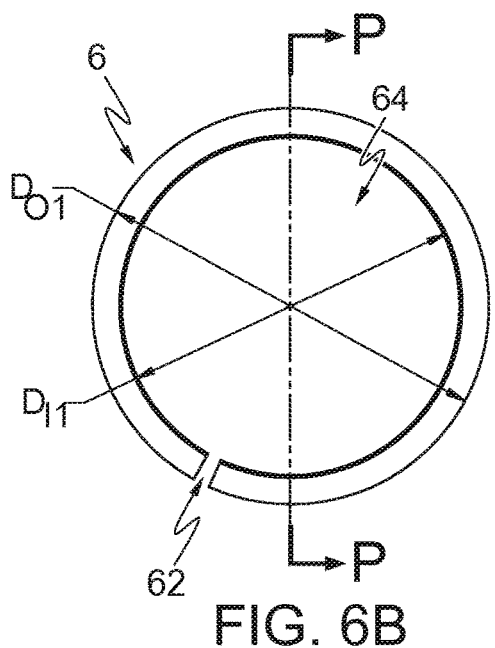
FIG. 6B is a top plan view of the locking ring of FIG. 6A, wherein the locking ring is in an unloaded state.
Figure 6C:
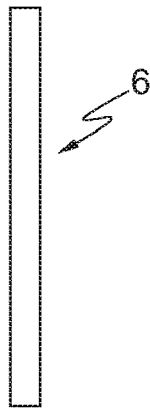
FIG. 6C is a right side elevational view of the locking ring of FIG. 6A.
Figure 6D:
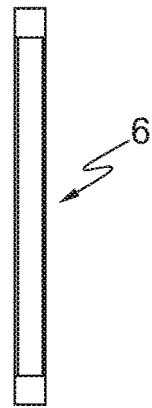
FIG. 6D is a cross section view of the locking ring of FIG. 6B, taken along line P-P.
Figure 6E:
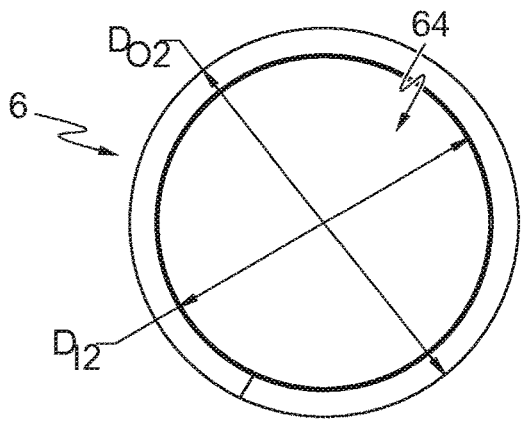
FIG. 6E is a top plan view of the locking ring of FIG. 6A, wherein the locking ring is in a loaded state.
Figure 7A:
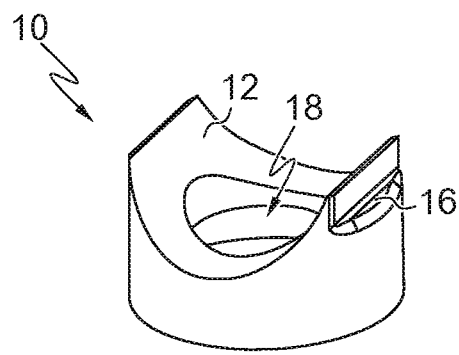
FIG. 7A is an isometric view of a rod seat of FIG. 1A.
Figure 7B:
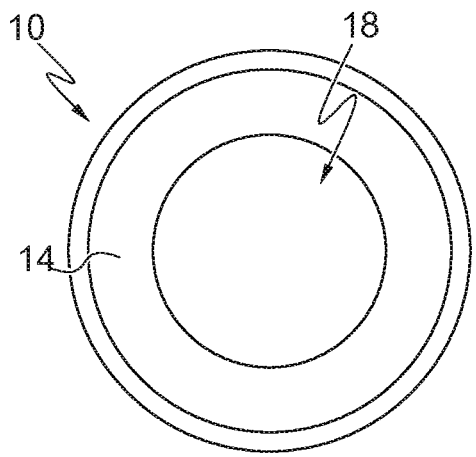
FIG. 7B is bottom plan view of the rod seat of FIG. 7A.
Figure 7C:
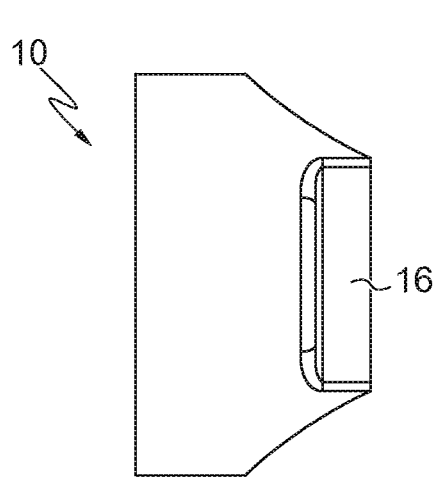
FIG. 7C is a right side elevational view of the rod seat of FIG. 7A.
Figure 7D:
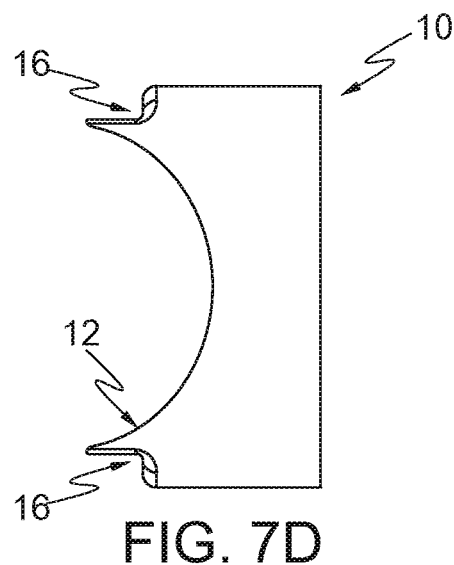
FIG. 7D is a front view of the rod seat of FIG. 7A.
Figure 7E:
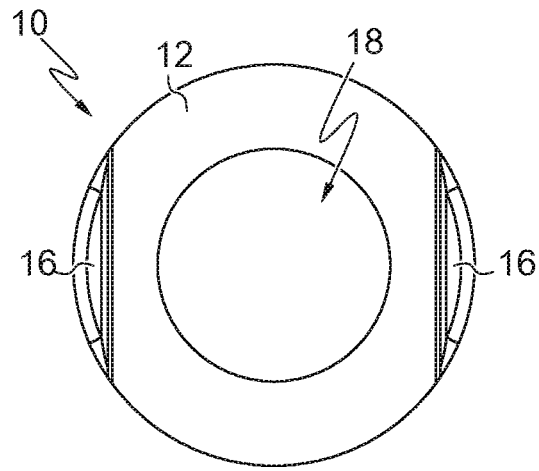
FIG. 7E is a top plan view of the rod seat of the FIG. 7A.
Figure 7F:
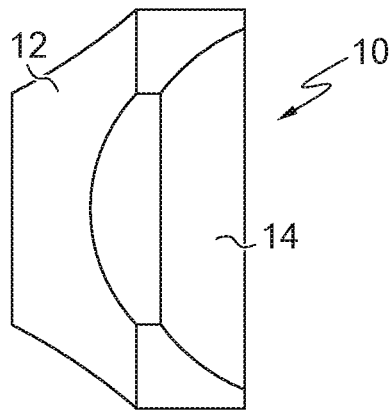
FIG. 7F is a cross sectional view of the rod seat of FIG. 7A.
Figure 8C:
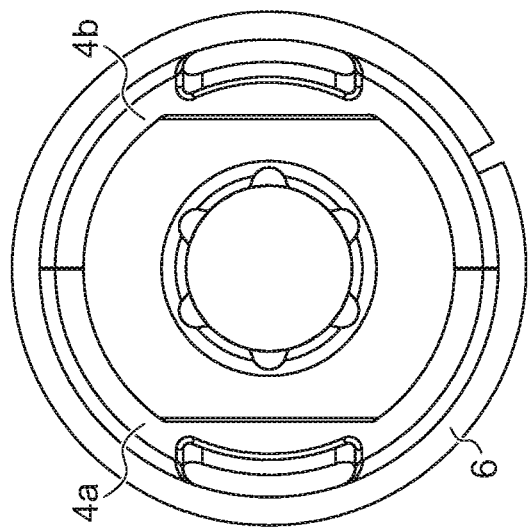
FIG. 8C is a top plan view of the screw shank of FIG. 8A.
Figure 8A:
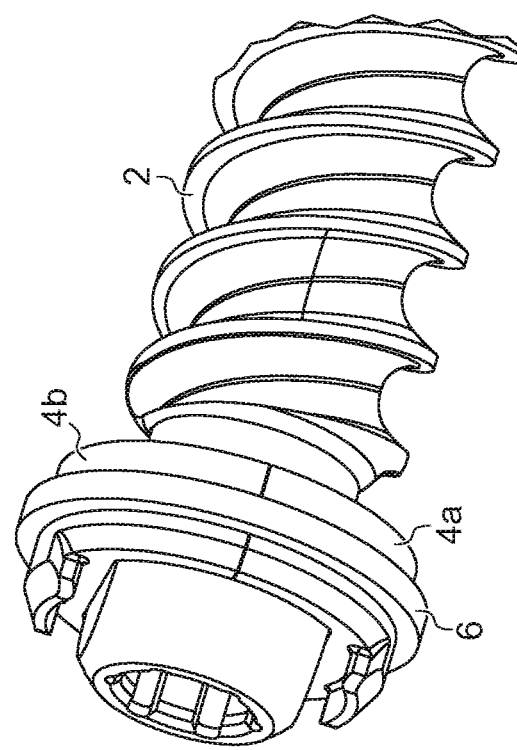
FIG. 8A is a partial isometric view of another embodiment of a screw shank of FIG. 1A.
Figure 8B:
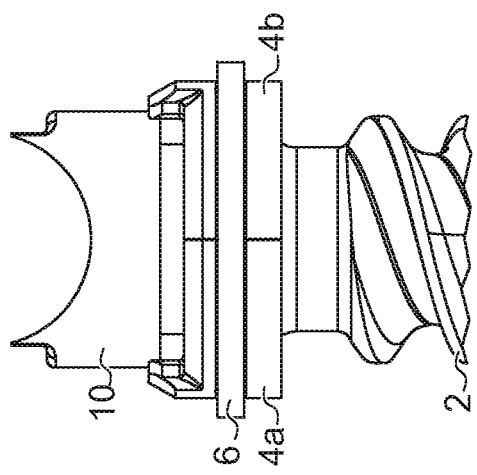
FIG. 8B is a side elevational view of the screw shank of FIG. 8A with the rod seat of FIG. 7A coupled thereon.
Figure 9A:
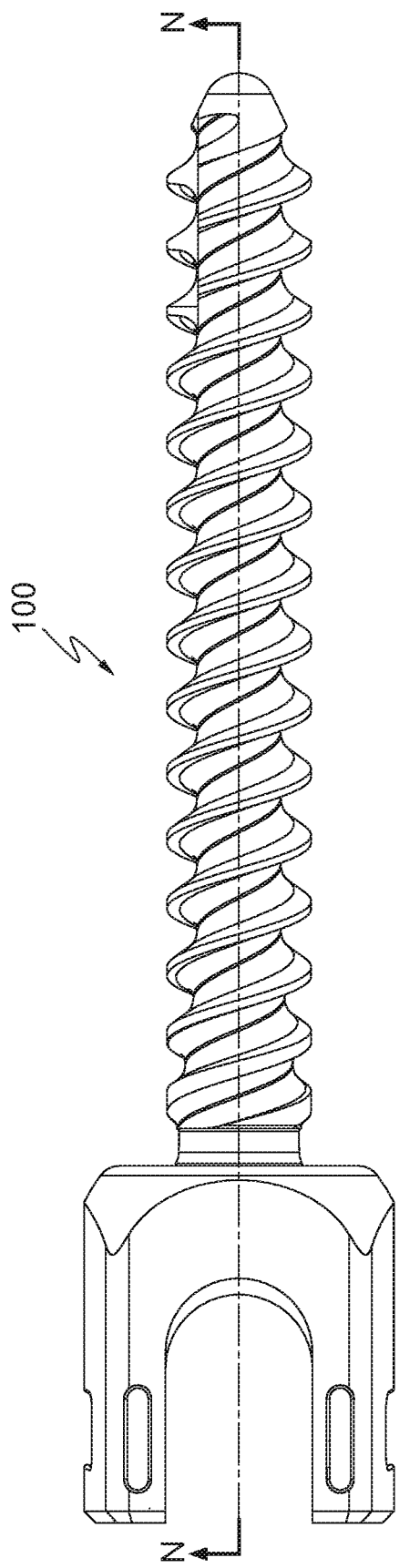
FIG. 9A is a side elevational view of another embodiment of a pedicle screw according to one or more embodiments.
Figure 9B:
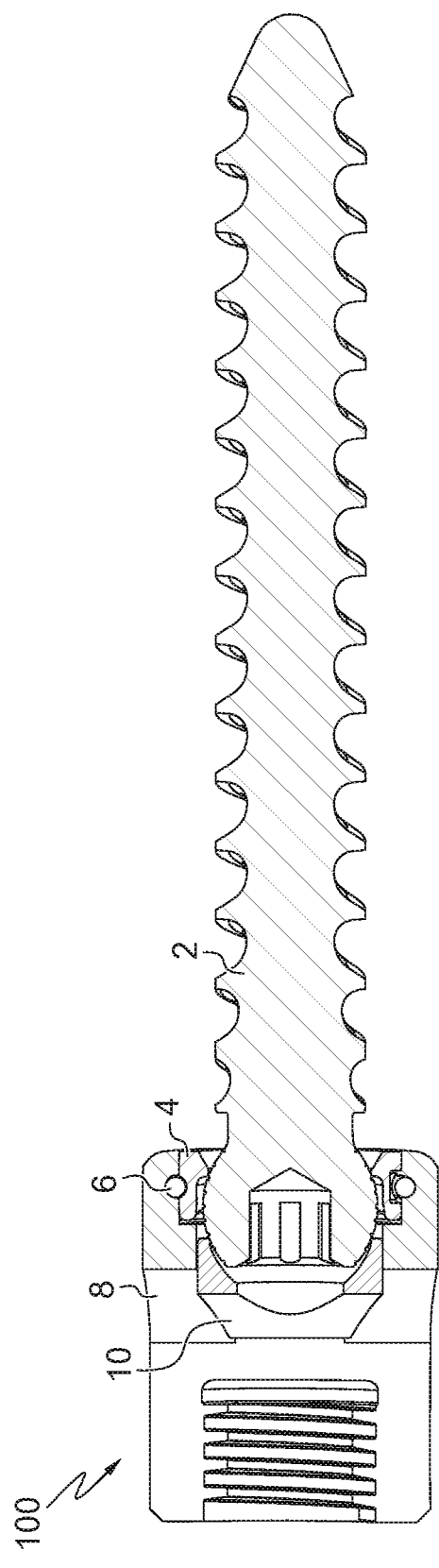
FIG. 9B is a cross sectional view of the pedicle screw of FIG. 9A, taken along line N-N.

Referring to FIGS. 5A-5F, one embodiment of the tulip head 8 is shown. Tulip head 8 defines an upper opening 81 and a lower opening 82. The upper opening 81 and lower opening 82 form a single cavity extending through the tulip head from the top end 83 to the bottom end 84. The lower opening 82 has a diameter ($D_{LO}$). Proximate to bottom end 84, an interior wall of the tulip head 8 comprises a retention groove 86 disposed therein. In an embodiment, the retention groove 86 forms a recessed channel with two side walls 87 and a bottom wall 88 as illustrated in FIGS. 1B and 5D-5E, for example. In another embodiment, the retention groove 86 forms a semicircular channel as shown, for example, in FIGS. 9B and 10D-10E. The retention groove 86 is sized and configured to accept the locking ring 6. In the illustrated embodiments, the retention groove 86 extends around the entire perimeter of lower opening 82 as illustrated in FIG. 5F representing a bottom view of tulip head 8 cut through retention groove 86.

In the illustrated embodiments, tulip head 8 includes a pair of anti-rotation sockets 90. The anti-rotation sockets are shaped and configured to mate with the anti-rotation tabs 32 of the retainer collar 4. When the retainer collar 4 is inserted into the lower opening 82 of the tulip head 8 the anti-rotation tabs 32 project into the anti-rotation sockets 90 and prevent relative rotational movement between the retainer collar 4 and the tulip head 8.

Tulip head 8, in the illustrated embodiment includes a pair of arms 91 which define a U-shaped channel 92 transverse to the single opening extending between upper opening 81 and lower opening 82. In an embodiment, internal threads 94 are formed in arms 91. The thread profile of internal threads 94 may be any profile known to one skilled in the art. Non-limiting examples of internal threads 94 include reverse angle threads, square threads, ACME threads, and buttress threads.

Referring to FIGS. 6A-6D and 11, locking ring 6 of pedicle screw 100 is shown. Locking ring 6 retains the tulip head 8 and the retainer collar 4 in an affixed position wherein axial movement is limited. In the illustrated embodiment, locking ring 6 has the form of a C-shaped spring or clip having a compression zone 62. The locking ring 6 comprises an annular geometry with a portion removed. The removed portion of the annular geometry forms the compression zone 62. The compression zone 62 of the locking ring 6 allows the locking ring 6 to be compressed into a reduced diameter arrangement. In the embodiment shown, locking ring 6 has an unloaded or natural state with an unloaded outer diameter ($D_{O1}$) and an unloaded inner diameter ($D_{I1}$) and a loaded or unnatural state with a loaded outer diameter ($D_{O2}$) and a loaded inner diameter ($D_{I2}$). The unloaded outer diameter ($D_{O1}$) and unloaded inner diameter ($D_{I1}$) represent diameters measured when locking ring 6 is under no contractive stress (i.e. no reduction in compression zone 62) or expansive stress (i.e. no expansion in compression zone 62). The loaded outer diameter ($D_{O2}$) and loaded inner diameter ($D_{I2}$) represent diameters measured when locking ring 6 is under a contractive stress (i.e. a reduction in compression zone 62).

The unloaded outer diameter ($D_{O1}$) is greater than the diameter ($D_{LO}$) of the lower opening 82 of tulip head 8. This arrangement retains the locking ring in the retention groove 86 when the locking ring 6 is in an unloaded or natural state. Additionally, the loaded outer diameter ($D_{O2}$) is less than the outer diameter ($D_{CO}$) of the retainer collar 4. This arrangement retains the locking ring in the locking ring groove 34 of the retainer collar 4 when the locking ring 6 is in an unloaded or natural state.

Referring to FIGS. 7A-7F, an embodiment of rod seat 10 is shown. Rod seat 10 functions to transfer force applied to a spinal rod disposed in the pedicle screw 100 to the spherical connector 22 of the screw shank 2. The rod seat 10 comprises a rod mating face 12 and a shank mating face 14. In an embodiment, the rod seat 10 further comprises a pair of retention ledges 16.

The rod mating face 12 is configured to accommodate the geometry of an elongated member, with the illustrated embodiment configured to mate with a spinal rod having a circular cross-sectional shape. Alternatively or additionally, the rod mating face 12 of rod seat 10 can have one or more other shapes to match elongated member geometries of differing diameter or shape. The shank mating face 14 is configured to accommodate the spherical connector 22 of the screw shank 2, and therefore the illustrated embodiment of shank mating face 14 has the shape of part of a sphere. Alternatively or additionally, the shank mating face 14 of rod seat 10 can have one or more other shapes to match differing spherical connector 22 geometries. In an embodiment, shank mating face 14 can be provided with a frictionor purchase-enhancing surface configuration (e.g. roughening or knurling) for cooperation with spherical connector 22 of the screw shank 2.

The illustrated embodiment of rod seat 10 also includes a hole 18 disposed therethrough. Hole 18 is provided so that the spherical connector 22 and, specifically, the driver receptacle 28, of screw shank 2 may be accessed through rod seat 10.

Rod seat 10 is sized and shaped to fit within at least chamber 96 of tulip head 8. The outer diameter of rod seat 10 is preferably slightly smaller than the inner diameter of chamber 96 and smaller than lower opening 82 so that rod seat 10 is slidably and rotatably movable within chamber 96 and lower opening 82. Further, in the illustrated embodiment the outer diameter of rod seat 10 is larger than the inner dimension of upper opening 81, so that rod seat 10 cannot move into upper opening 81. The cavity 89 such as, for example, chamber 96, may include a stop that extends inwardly from the interior wall of the cavity 89 sufficient enough to engage a corresponding stop on the rod seat 10 to prevent the rod seat from moving into the upper portion of the cavity 89 and/or the upper opening 81. The cavity stop(s) may be disposed above the retention groove 86 but below the upper opening 81 and/or upper cavity. Specifically, in the illustrated embodiment, retention ledges 16 (i.e., stops of the rod seat 10) mate with the upper face of chamber 96 (i.e., stops of the cavity 89) to prevent movement of rod seat 10 into upper opening 81. It is understood that other embodiments and configurations of the corresponding stops may be used to prevent the rod seat 10 from moving into the upper cavity and/or the upper opening. Further, in the illustrated embodiment, the retention ledges 16 mate with arms 91 to prevent rotation of the rod seat 10 relative to the tulip head 8.

Generally referring to FIGS. 1A-1C, 8A-8C, 9A-9B, 12 and 13D, an embodiment of a method of assembling the pedicle screw 100 may generally include assembling rod seat 10 and retainer collar 4 adjacent to and/or partially or entirely about connector 22 of screw shank 2 and inserting locking ring 6 into locking ring groove 34 to form a subassembly, and then subsequently inserting the subassembly into the lower opening 82 of the tulip head until the locking ring 6 snaps into and/or engages retention groove 86.

In some embodiments, the screw shank 2, rod seat 10, retainer collar 4, and locking ring 6 may each be inserted into tulip head 8 individually. For example, the method may include inserting the rod seat 10 into lower opening 82 of tulip head 8 first and then subsequently inserting the locking ring 6 into lower opening 82 until locking ring 6 snaps into and/or engages retention groove 86. The method may further include placing the retainer collar 4 about a portion of or entirely about the connector 22, and then subsequently, inserting the retainer collar 4 and screw shank 2 subassembly into lower end 82 until the locking ring 6 snaps into and/or engages locking ring groove 34 of the subassembly.

In another example, a method may include placing retainer collar 4 partially or entirely about the spherical connector 22 to form a subassembly, snapping and/or engaging locking ring 6 into locking ring groove 34 around the retainer collar 4, inserting the rod seat 10 into lower opening 82 of tulip head 8 first and next inserting screw shank 2, retainer collar 4, and locking ring 6 subassembly into lower opening 82 until the locking ring engages and/or snaps into the retention groove 86 within the cavity of tulip head 8.

In one specific embodiment, retainer collar 4 are fitted around the spherical connector 22 of screw shank 2 and locking ring 6 is fitted into locking ring groove 34 of retainer collar 4 prior to insertion of screw shank 2 into tulip head 8. In an embodiment, retainer collar 4 can be placed around spherical connector 22 of screw shank 2 by placing the two semicircular collar halves 4a/4b of retainer collar 4 on opposed sides of the spherical connector 22. In another embodiment, the retainer collar 4 can be placed around spherical connector 22 of screw shank 2 by expanding the diameter of screw shank pass-through aperture 48 to fit over the spherical connector 22. The multi-piece nature of retainer collar 4 allows screw shank pass-through aperture 48 to be smaller than spherical connector 22. Locking ring 6 can be placed around retainer collar 4 and screw shank 2 by inserting the spherical connector 22 with the retainer collar 4 disposed thereon through locking ring pass-through aperture 64 of locking ring 6. Passage of retainer collar 4 through locking ring pass-through aperture 64 causes compression zone 62 to expand thereby enlarging unloaded inner diameter $D_{I1}$ of locking ring 6 to accommodate passage of retainer collar 4. Upon alignment of locking ring 6 with locking ring groove 34, locking ring 6 contracts inwardly back to its normal state, i.e. compression zone 62 contracts, thereby reducing the inner diameter of locking ring 6 back to its unloaded state and unloaded diameter $D_{I1}$ and thus securing locking ring 6 into locking ring groove 34 of retainer collar 4. In an embodiment, retention of locking ring 6 into locking ring groove 34 also retains the halves of retainer collar 4 around spherical head 22 of screw shank 2. Subsequently, compression zone 62 of locking ring 6 may be reduced once again via compressing locking ring 6 inwardly beyond its normal state (unloaded state), thereby reducing unloaded outer diameter $D_{O1}$ of locking ring 6. While in a compressed configuration, the assembly of locking ring 6, retainer collar 4, and screw shank 2 are inserted into tulip head 8 through lower opening 82. Upon alignment of locking ring 6 with retention groove 86 of tulip head 8, compression of locking ring 6 is allowed to release, locking ring 6 expands, and locking ring 6 is secured into retention groove 86. Securing of locking ring 6 also retains retainer collar 4 and screw shank 2 in the tulip head 8.

Alternatively, compression zone 62 of locking ring 6 may be reduced thereby reducing unloaded outer diameter $D_{O1}$ of locking ring 6. While in a compressed configuration, locking ring 6 is inserted into tulip head 8 through lower opening 82. Upon alignment with retention groove 86 of tulip head 8, compression of locking ring 6 is allowed to release, locking ring 6 expands back to its unloaded outer diameter $D_{O1}$, and locking ring 6 is secured into retention groove 86. Subsequently, screw shank 2 having retainer collar 4 disposed around spherical connector 22 is inserted into tulip head 8 through lower opening 82. Upon contact with locking ring 6, the retainer collar 4 forces expansion of the unloaded inner diameter $D_{I1}$ of locking ring 6 such that retainer collar 4 is allowed to pass through. Upon alignment of locking ring 6 with locking ring groove 34, compression zone 62 contracts thereby reducing the inner diameter of locking ring 6 back to its unloaded inner diameter $D_{I1}$ and securing locking ring 6 into locking ring groove 34 of retainer collar 4. Securing of retainer collar 4 by the locking ring 6 also retains screw shank 2 in the tulip head 8.

Prior to insertion of the screw shank 2, retainer collar 4, or locking ring 6 into the tulip head 8, rod seat 10 is inserted into tulip head 8 through lower opening 82. Rod seat 10 remains slideably and rotatably positioned in chamber 96 of tulip head 8, and screw shank 2 remains moveable with respect to tulip head 8 and rod seat 10. Movement of screw shank 2 in a poly-axial or uni-axial manner in relation to tulip head 8 and rod seat 10 depends on the configuration of spherical connector 22. In a poly-axial arrangement of spherical connector 22, where spherical connector 22 retains a curved profile around the entire periphery, the screw shank 2 may move in a poly-axial manner. In a uni-axial arrangement of spherical connector 22, where spherical connector 22 has flat angulation guides 26, the screw shank 2 may move in a uni-axial manner. However, in poly-axial configurations and uni-axial configurations without anti-rotation tabs 32 on the retainer collar 4, screw shank 2 may rotate about a longitudinal axis of the screw shank 2 relative to the tulip head 8.

In one specific embodiment the diameter of retention groove 86 of tulip head 8 is smaller than the unloaded outer diameter $D_{O1}$ of locking ring 6 in its natural (i.e., unloaded) state. Thus, when locking ring 6 is within retention groove 86, locking ring 6 is continually under a compressive force and presses against the bottom wall 88 of retention groove 86. Alternatively, the diameter of retention groove 86 may be the same size or slightly larger than the unloaded outer diameter $D_{O1}$ of locking ring 6. If the diameter of retention groove 86 is the same size or slightly larger than the unloaded outer diameter $D_{O1}$ of locking ring 6, locking ring 6 rests upon a side wall 87 of retention groove 86 which holds locking ring 6 within retention groove 86. The depth of retention groove 86 is less than the width of locking ring 6, so that when locking ring 6 is disposed in retention groove 86, a portion of locking ring 6 projects into chamber 96 proximal to lower opening 82. In some embodiments, the width of locking ring 6 is equivalent to the difference between the unloaded outer diameter $D_{O1}$ and the unloaded inner diameter $D_{I1}$.

When locking ring 6 is seated within retention groove 86 and locking ring groove 34, screw shank 2 and rod seat 10 are retained within lower opening 82 of tulip head 8. Rod seat 10 is supported by spherical connector 22 of screw shank 2, and spherical connector 22 is supported by spherical connector mating surfaces 36 of retainer collar 4. In an embodiment, retainer collar 4 is held around spherical connector 22 by locking ring 6 disposed in locking ring groove 34. Locking ring 6 is held by retention groove 86 of tulip head 8 and, thus, screw shank 2, retainer collar 4, and rod seat 10 are held in tulip head 8.

Preferably, pedicle screw 100 is assembled (as described above) prior to use in a surgical procedure. Alternatively, it is envisioned that all or a portion of assembly may be completed in the operating theater. The bottom loading aspect of the assembly wherein the screw shank 2 is inserted into the tulip head 8 through lower opening 82 allows the same tulip head 8 to be used for screw shanks 2 of various thread diameter and/or pitch. A standard dimension of the spherical connector 22 is utilized for screw shanks 2 of different diameters and because the threaded portion of the screw shank 2 does not have to pass through tulip head 8 the geometry of tulip head 8 may be consistent.

The bottom loading configuration of pedicle screw 100 during the assembly process also allows for an overall lower profile tulip head 8.

In using the illustrated embodiment of pedicle screw 100, screw shank 2 of pedicle screw 100 is threaded into an appropriately prepared hole in a bone (not shown). The threaded portion of screw shank 2 is inserted into the hole, and an appropriate screwing tool is used with driver receptacle 28 of screw shank 2 through hole 18 in rod seat 10, and screw shank 2 is threaded into the bone. When screw shank 2 has been threaded into the bone to the desired depth, tulip head 8 is positioned so that upper opening 81 forms a desired angle with screw shank 2 and U-shaped channel 92 is oriented in the desired direction. An elongated member such as a spinal rod, connector, or other orthopedic surgical implant is coupled with pedicle screw 100 by placing the elongated member in U-shaped channel 92 of tulip head 8 such that it contacts rod mating face 12 of rod seat 10. A compression member, such as a set screw or threaded plug, is threaded into internal threads 94 of tulip head 8 to secure the elongated member. As the compression member is tightened, elongated member is forced downward against rod seat 10, which pushes shank mating face 14 of rod seat 10 down onto spherical connector 22 of screw shank 2. Spherical connector 22 is thereby clamped between shank mating face 14 of rod seat 10 and spherical connector mating surface 36 or spherical connector mating edge 52 of retainer collar 4. In this way, screw shank 2 is locked into the desired angular position with respect to elongated member and the remainder of pedicle screw 100.

Referring to FIGS. 14-27, another embodiment of a pedicle screw 200 is shown. The pedicle screw 200 includes a screw shank 2, retainer collar 204, locking ring 206, tulip head 208, and rod seat 210. When assembled together, these components form pedicle screw 200. Each of the components set forth above will be individually described below herein and, in some cases, shown in separate figures. In addition, it will be shown and described below herein how each of the components of the pedicle screw 200 are interconnected and, once assembled, how the pedicle screw 200 works in operation. In this embodiment, the screw shank 2 is the same as the screw shank 2 described above herein and shown, for example, in FIGS. 2A-2D and 13A-13B, which is hereby incorporated by reference herein.

Figure 15:
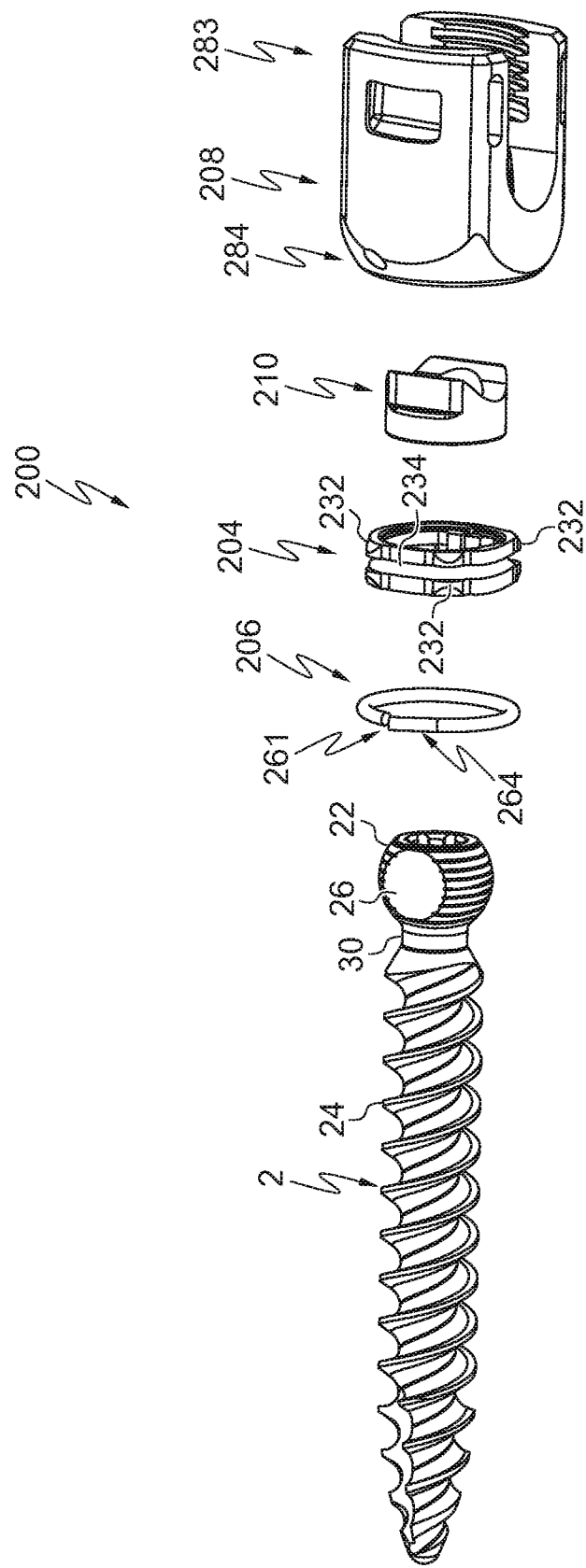
FIG. 15 is an exploded view of the pedicle screw of FIG. 14.

Referring to FIG. 15, locking ring 206 of pedicle screw 200 is shown. Locking ring 206 in this embodiment is a wire formed into an annular ring having a locking ring pass-through aperture 264. As shown, the locking ring 206 includes a gap 261 between opposite ends of the wire. The wire may be fabricated from a variety of metals, alloys, and/or composites. In one example, the wire is fabricated from cobalt-chromium (CoCr) or the like, including but not limited to cobalt-chromium-molybdenum (CoCrMo), cobalt-nickel-chromium-molybdenum (CoNiCrMo). In some examples, the locking ring 206 is fabricated form materials such as, for example, metal alloys with high wear-resistance and biocompatibility.

Figure 16:
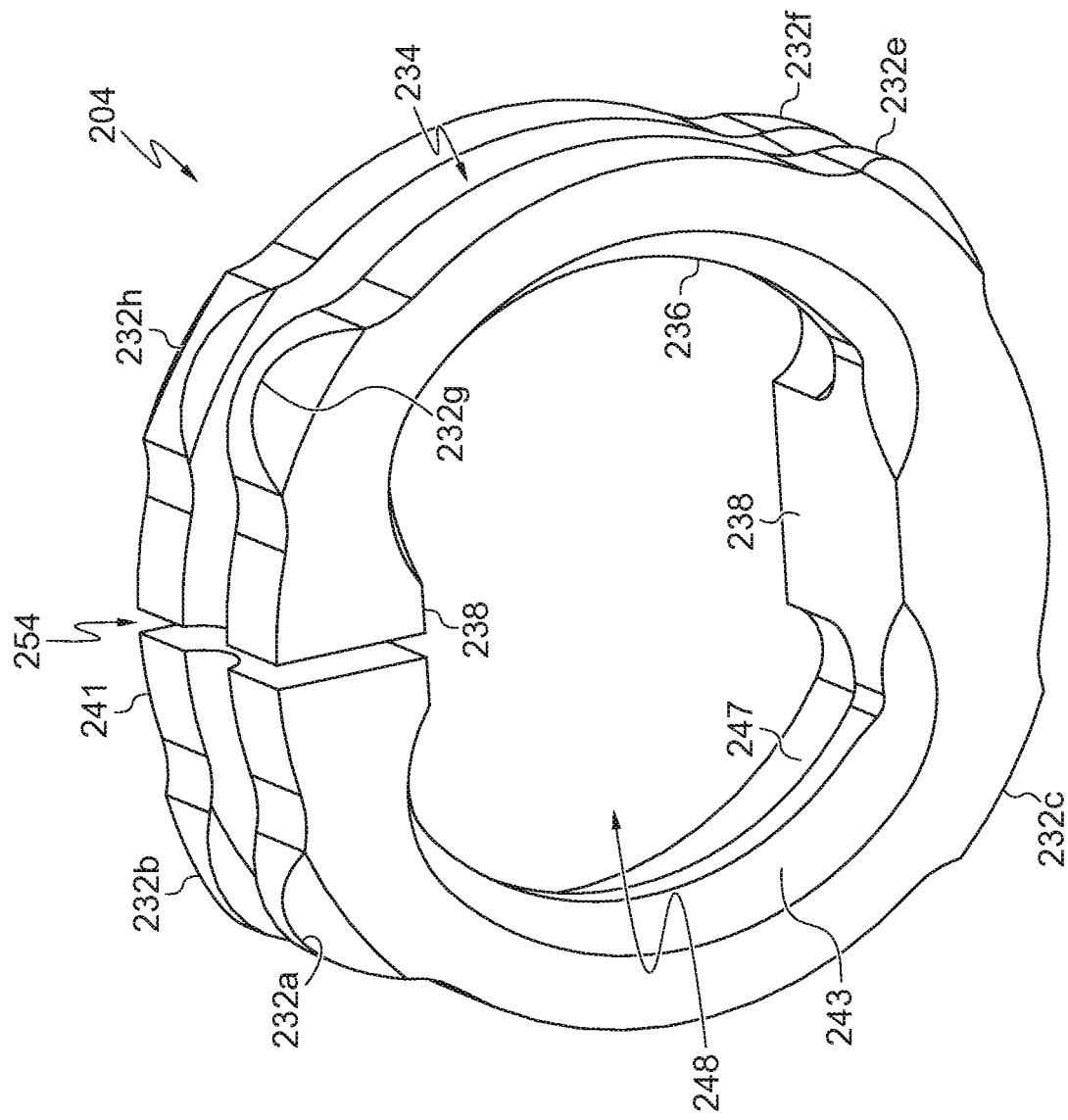
FIG. 16 is an isometric view of a retainer collar of FIG. 14.
Figure 17:
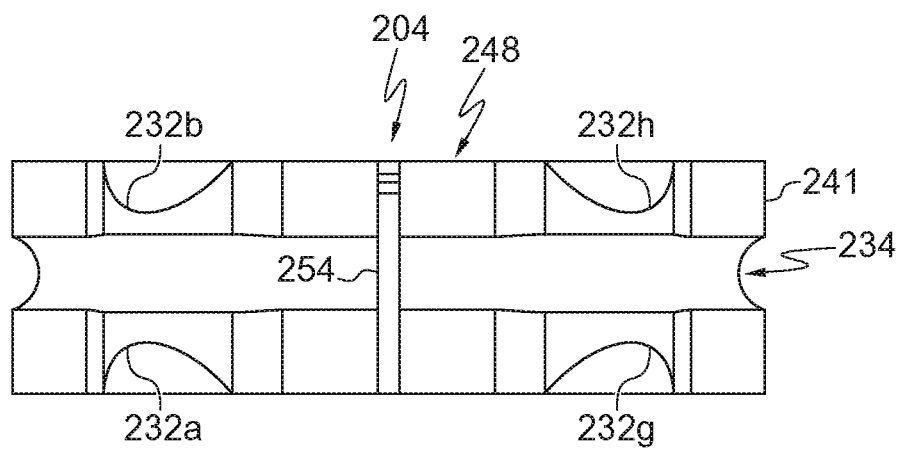
FIG. 17 is a side elevational view of the retainer collar of FIG. 16.
Figure 18:
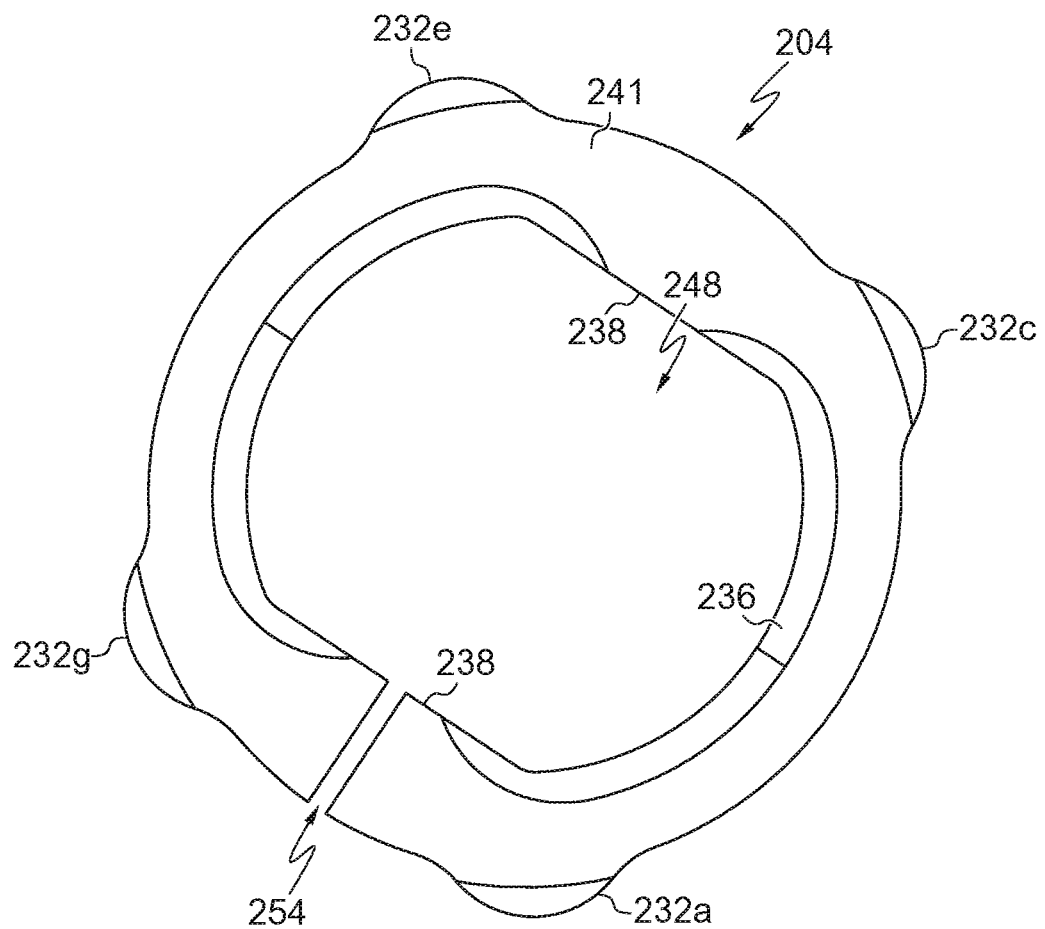
FIG. 18 is a bottom plan view of the retainer collar of FIG. 16.

Referring to FIGS. 16-18, retainer collar 204 of pedicle screw 200 is shown. In various embodiments, the retainer collar 204 comprises an annular body 241 having a collar split 254 that may or may not allow the annular body to expand and/or contract in its diameter. In some embodiments, the retainer collar 204 may comprise embodiments as shown and described above herein such as, for example, retainer collar 4. In the embodiment shown in FIGS. 16-18, the retainer collar 204 includes a locking ring groove 234 disposed within an outer surface of annular body 241. The locking ring groove 234 is shown as disposed continuously around the annular body 241, forming a recessed channel. In this embodiment, locking ring groove 234 has a semicircular profile. However, it is understood that locking ring groove 234 does not need to be continuous or completely encircle the annular body 241. In addition, locking ring groove 234 may comprise a variety of shapes, sizes, configurations, profiles, and designs, but is generally shaped and sized to accept locking ring 206.

The annular body 241 also includes anti-rotation tabs 232a, 232c, 232e, and 232g and anti-rotation tabs 232b, 232d, 232f, and 232h that are disposed on a side of the locking ring groove 234 opposite from anti-rotation tabs 232a, 232c, 232e, and 232g, respectively. As shown, the anti-rotation tabs 232a-h radially project from the annular body 241 and are configured to mate with corresponding anti-rotation sockets 290a-h, respectively, disposed in the tulip head 208 as will be described below herein.

In a uni-axial pedicle screw 200, prevention of rotation of the retainer collar 204 in turn prevents rotation of the screw shank 2 relative to tulip head 208. Rotation of screw shank 2 relative to tulip head 208 in a uni-axial screw is generally not desirable as the direction of pivot would also rotate. In an embodiment of a uni-axial pedicle screw 200, anti-rotation tabs 232a-h are omitted to allow angulation and manipulation of tulip head 208 after insertion of screw shank 2 into a patient's bone. In a poly-axial pedicle screw 200 rotation of the screw shank 2 relative to the tulip head 208 is not generally a concern so the anti-rotation tabs 232a-h may be omitted or retained.

In an embodiment, the interior surface of the retainer collar 204 includes a spherical connector mating surface 236 sized and configured to interface and mate with the spherical connector 22 of the screw shank 2. In an embodiment, specifically a poly-axial pedicle screw 200, the spherical connector mating surface 236 comprises a curved surface matching the curved profile of the spherical connector 22 and the curved profile extends the full 360° profile of the interior surface of the retainer collar 204. In another embodiment, specifically a uni-axial pedicle screw 200, the spherical connector mating surface 236 comprises a curved surface matching the curved profile of the spherical connector 22 as well as flat planar surfaces 238 matching the angulation guides 26 of the spherical connector 22 as shown in FIGS. 16, 18, 24, and 26. The arrangement of the curved profile and planar surfaces match the arrangement of the spherical portions and the angulation guides 26 of the spherical connector 22.

The retainer collar 204 retains the spherical connector 22 of the screw shank 2. A screw shank pass-through aperture 248 is formed in retainer collar 204. The screw shank pass-through aperture 248 is sized to fit around the shank collar 30 of the screw shank 2 but prevent passage of the spherical connector 22. In an embodiment, the screw shank pass-through aperture 248 is formed by the annular body 241 of the retainer collar 204. In some embodiments, the retainer collar 204 may comprise a spherical connector mating edge such as, for example, mating edge 52 described above herein and shown in FIG. 10A.

Figure 19:
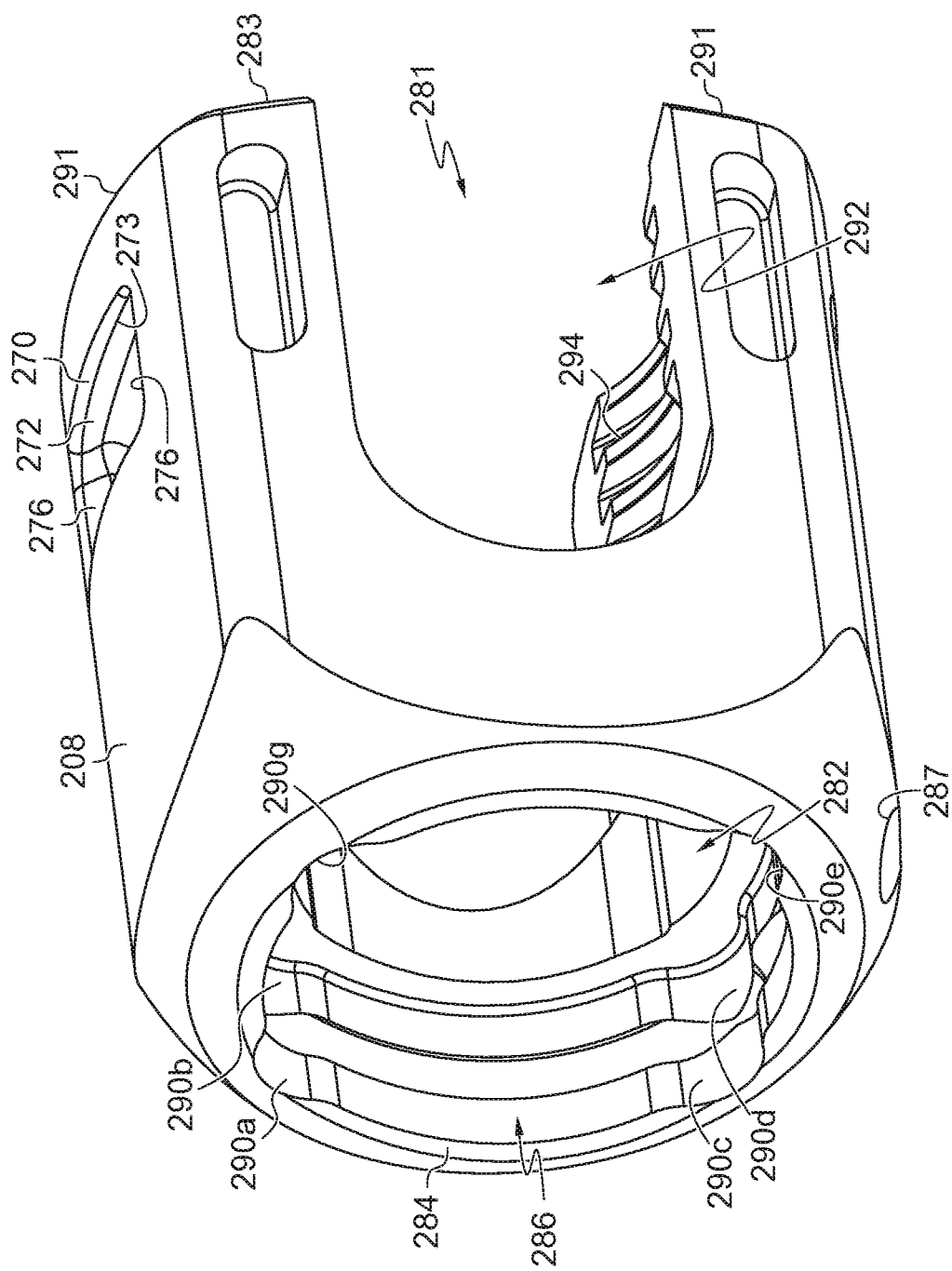
FIG. 19 is an isometric view of a tulip head of FIG. 14.
Figure 20:
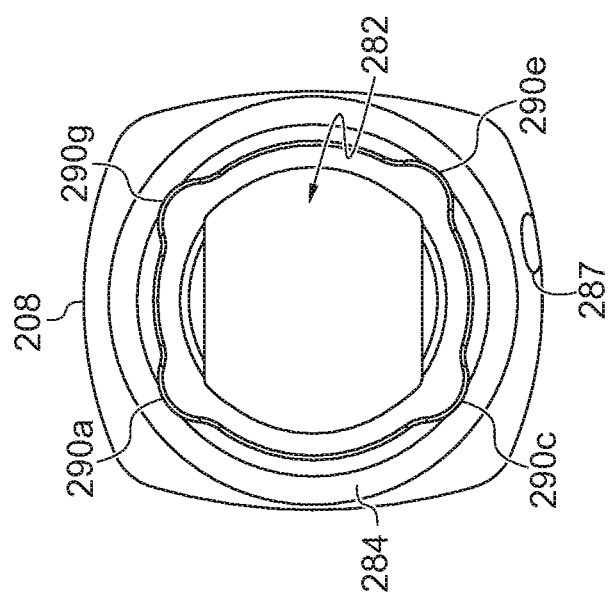
FIG. 20 is a bottom plan view of the tulip head of FIG. 19.
Figure 23:
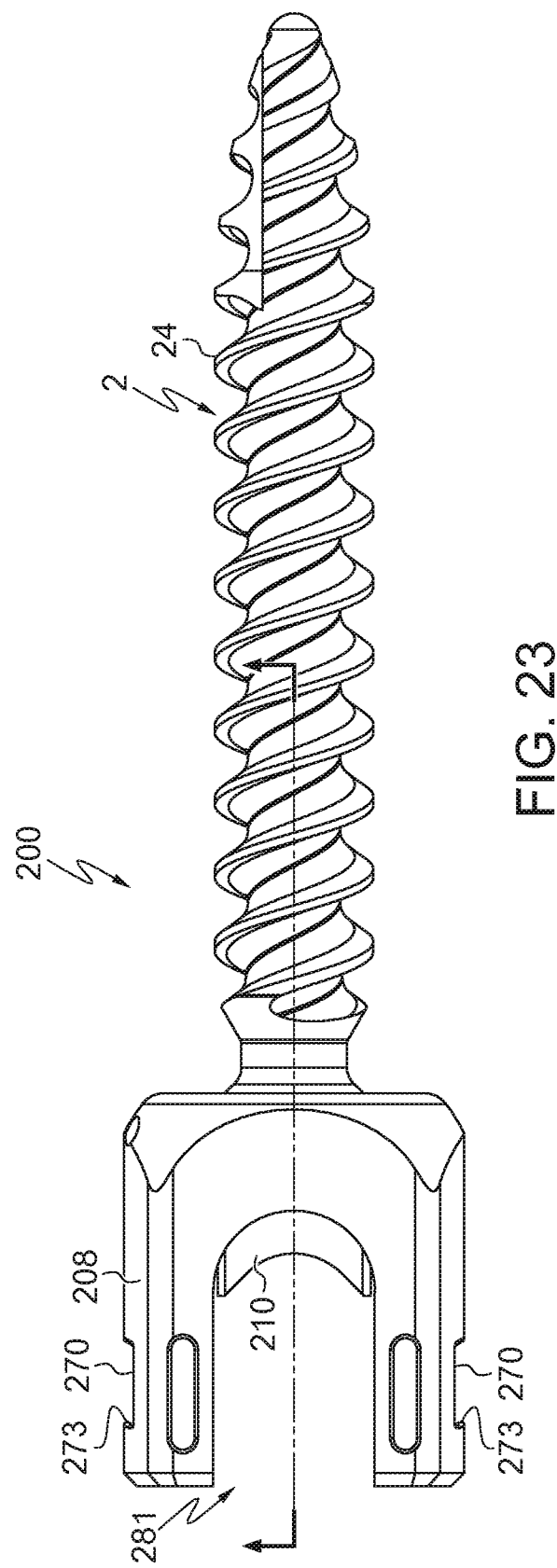
FIG. 23 is a side elevational view of the pedicle screw of FIG. 14.
Figure 24:
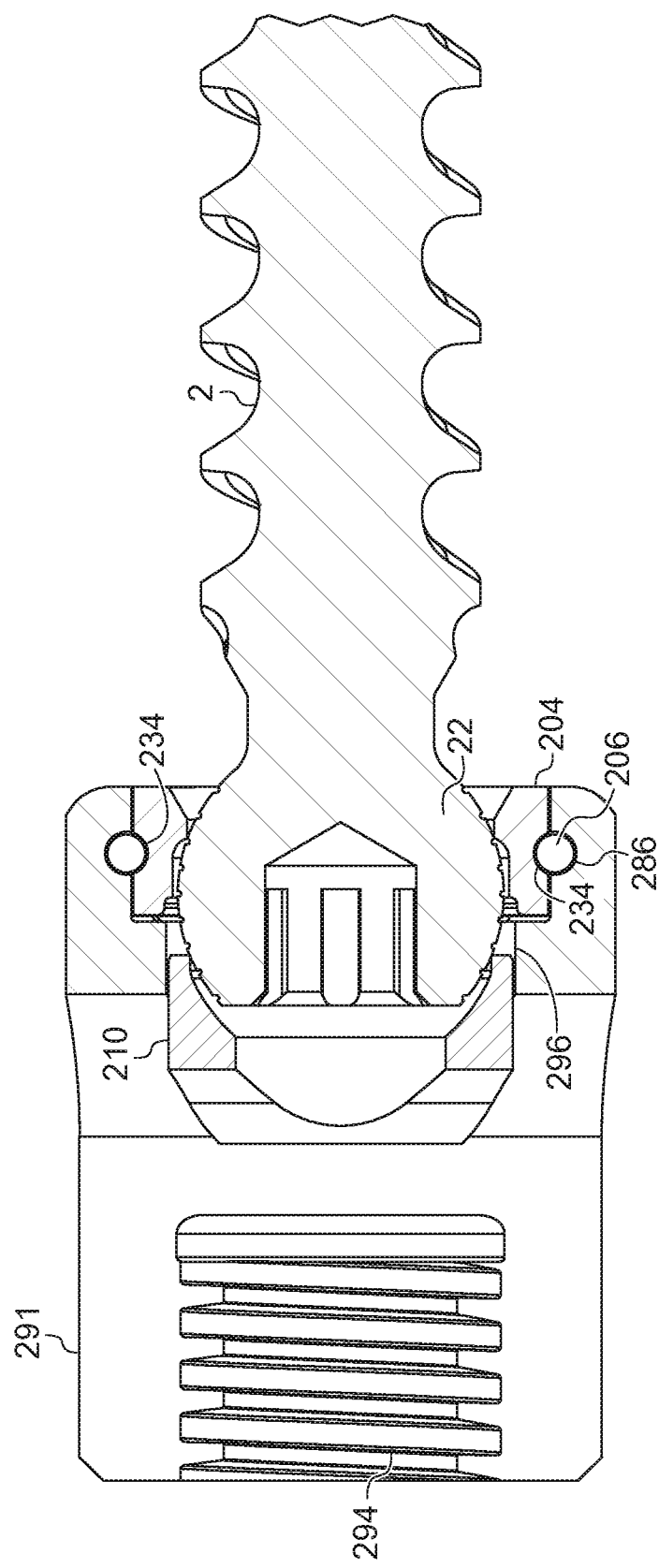
FIG. 24 is a partial cross sectional view of the pedicle screw of FIG. 23, taken along line O-O.
Figure 25:
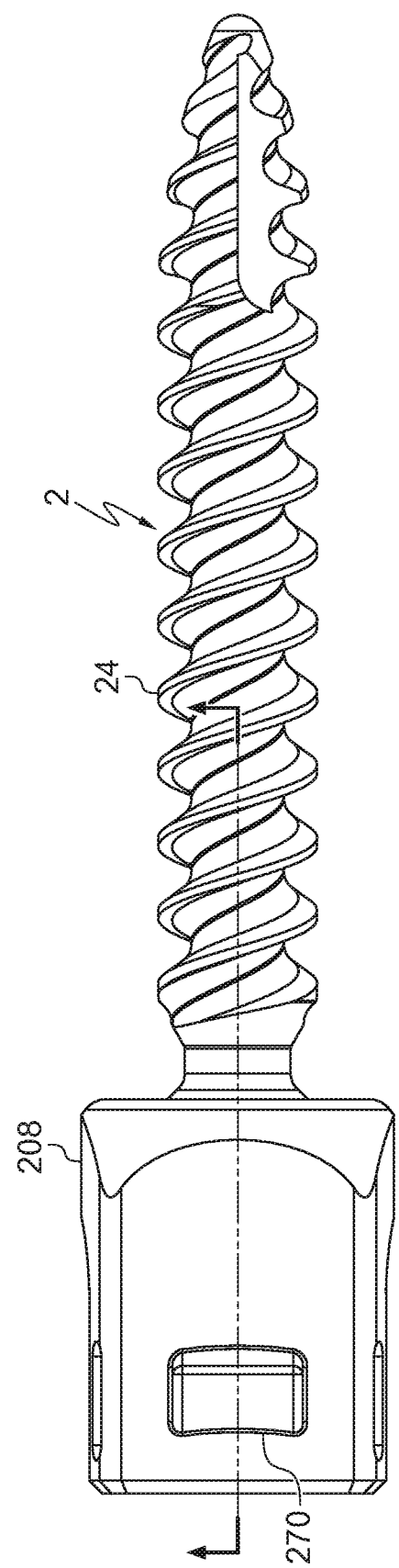
FIG. 25 is a side elevational view of the pedicle screw of FIG. 14.
Figure 26:
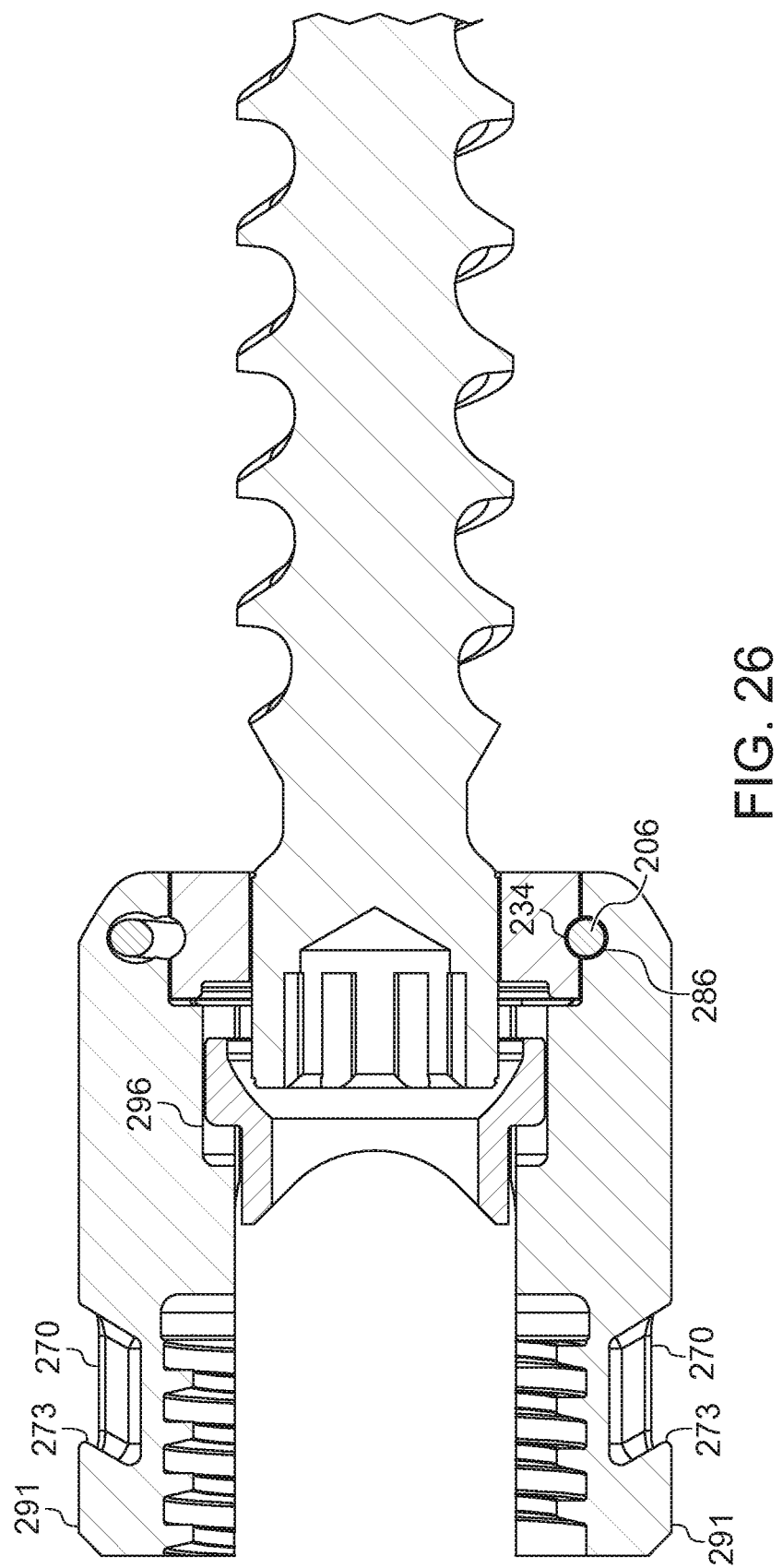
FIG. 26 is a partial cross sectional view of the pedicle screw of FIG. 25, taken along line P-P.
Figure 27:
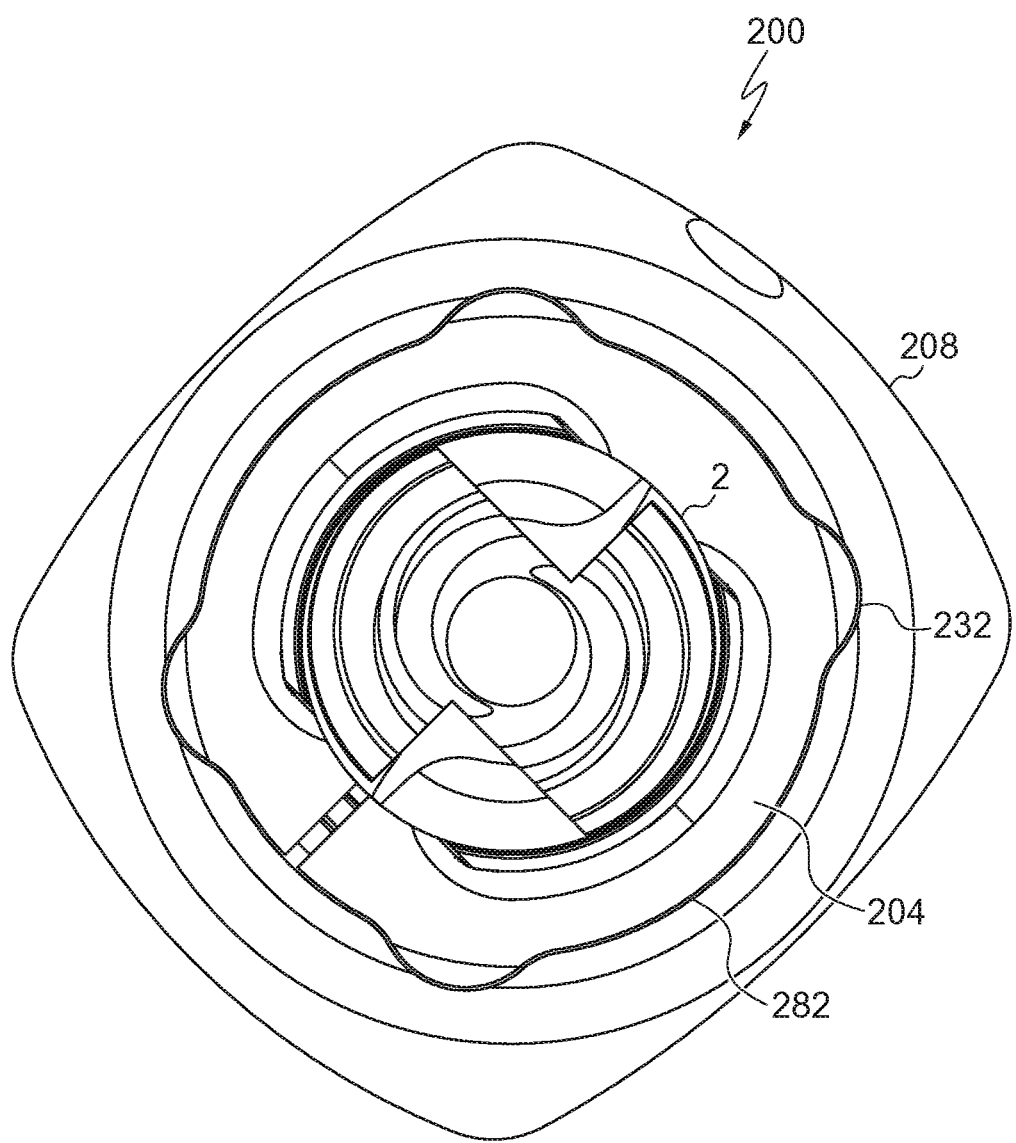
FIG. 27 is a bottom plan view of the pedicle screw of FIG. 14.

Referring to FIGS. 19-20, one embodiment of the tulip head 208 is shown. Tulip head 208 defines an upper opening 281 and a lower opening 282. The upper opening 281 and lower opening 282 form a single cavity extending from the top end 283 to the bottom end 284. Proximate to bottom end 284, the tulip head 208 comprises a retention groove 286. In this embodiment, retention groove 286 has a semicircular profile as illustrated in FIGS. 19, 24, and 26, for example. In another embodiment, the retention groove 86 may include two side walls and a bottom wall such as, for example, those shown and described above herein with reference to FIGS. 5D-5E. The retention groove 286 is sized and configured to accept the locking ring 206. In the illustrated embodiments, the retention groove 286 extends around the entire perimeter of lower opening 282 and is in communication and/or connected with a retention groove inlet 287 that extends to an exterior surface of the tulip head 208. The retention groove inlet 287 is configured and sized to accept and/or receive the locking ring 206 and permit the locking ring 206 to travel therethrough and enter into the retention groove 286.

In the illustrated embodiments, tulip head 208 includes a pair of anti-rotation sockets 290a-h. The anti-rotation sockets 290a-h are shaped and configured to mate with the respective anti-rotation tabs 232a-h of the retainer collar 204. When the retainer collar 204 is inserted into the lower opening 282 of the tulip head 208 the anti-rotation tabs 232a-h project into the respective anti-rotation sockets 290a-h and prevent relative rotational movement between the retainer collar 204 and the tulip head 208.

Tulip head 208, in the illustrated embodiment includes a pair of arms 291 which define a U-shaped channel 292 transverse to the single opening extending between upper opening 281 and lower opening 282. In an embodiment, internal threads 294 are formed in arms 291. The thread profile of internal threads 294 may be any profile known to one skilled in the art. Non-limiting examples of internal threads 294 include reverse angle threads, square threads, ACME threads, and buttress threads. These threads 294 may be configured to receive and threadingly engage an externally threaded set screw. In an embodiment, each arm 291 of the tulip head 208 further includes a tulip head pocket 270 as shown, for example, in FIGS. 14, 19, and 26. In the embodiment shown, the tulip head pockets 270 of the tulip head 208 do not extend transversely all the way across the tulip head 208. Thus, in this illustrative embodiment, the tulip head pockets 270 each have an upper wall 272 that includes a tulip head undercut 273, a lower wall 274, two opposed side walls 276, and a back wall 278 disposed between the two opposed side walls 276. In an embodiment, the tulip head pockets 270 and, more specifically, the tulip head undercuts 273 are constructed to engage various orthopedic surgical tools configured to facilitate installation, removal, and/or adjustment of the pedicle screw 200.

Figure 22:
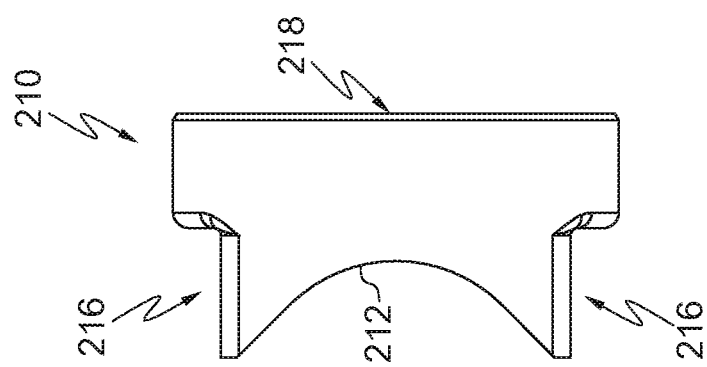
FIG. 22 is a front view of the rod seat of FIG. 21.
Figure 21:
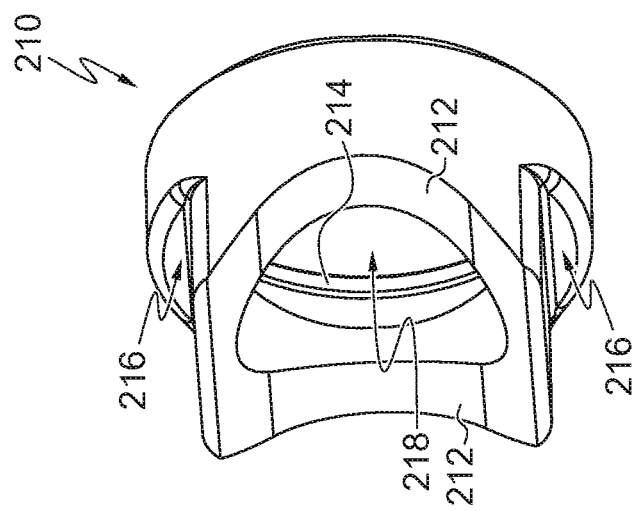
FIG. 21 is an isometric view of a rod seat of FIG. 14.

Referring to FIGS. 21-22, an embodiment of rod seat 210 is shown. Rod seat 210 functions to transfer force applied to a spinal rod (not shown) disposed in the U-shaped channel 292 of pedicle screw 200 to the spherical connector 22 of the screw shank 2. The rod seat 210 comprises a rod mating face 212 and a shank mating face 214. In an embodiment, the rod seat 210 further comprises a pair of retention ledges 216.

The rod mating face 212 is configured to accommodate the geometry of an elongated member, with the illustrated embodiment configured to mate with a spinal rod having a circular cross-sectional shape. Alternatively or additionally, the rod mating face 212 of rod seat 210 may have one or more other shapes to match elongated member geometries of differing diameter or shape. The shank mating face 214 is configured to accommodate the spherical connector 22 of the screw shank 2, and therefore the illustrated embodiment of shank mating face 214 has the shape of a portion of a sphere. Alternatively or additionally, the shank mating face 214 of rod seat 210 may have one or more other shapes to match differing spherical connector 22 geometries. In an embodiment, shank mating face 214 may be provided with a friction- or purchase-enhancing surface configuration (e.g. roughening or knurling) for cooperation with spherical connector 22 of the screw shank 2.

The illustrated embodiment of rod seat 210 also includes a hole 218 disposed therethrough. Hole 218 is provided so that the spherical connector 22, and specifically, the driver receptacle 28, of screw shank 2 may be accessed through rod seat 210. Rod seat 210 is sized and shaped to fit within at least chamber 296 of tulip head 208. The outer diameter of rod seat 210 is preferably slightly smaller than the inner diameter of chamber 296 and smaller than lower opening 282 so that rod seat 210 is slidably and rotatably movable within chamber 296 and lower opening 282. Further, in the illustrated embodiment the outer diameter of rod seat 210 is larger than the inner dimension of upper opening 281, so that rod seat 210 cannot move into upper opening 281. Specifically, in the illustrated embodiment, retention ledges 216 mate with the upper face of chamber 296 to prevent movement of rod seat 210 into upper opening 281. Further, in the illustrated embodiment, the retention ledges 216 mate with arms 291 to prevent rotation of the rod seat 210 relative to the tulip head 208.

Generally referring to FIGS. 14-27, pedicle screw 200 is assembled as follows: screw shank 2, rod seat 210, and retainer collar 204 are inserted into tulip head 208 through bottom end 284. The screw shank 2, rod seat 210, and retainer collar 204 may be inserted into tulip head 208 either individually or substantially in a single step. For example, the rod seat 210 may be inserted into the bottom end 284 of tulip head 208 first, followed by screw shank 2, and then the retainer collar 204 may be slid around the spherical connector 22 and into the bottom end 284 of the tulip head 208. Alternatively, the rod seat 210 may be inserted into tulip head 208 first, followed by screw shank 2 with retainer collar 204 which has been already placed around the spherical connector 22. In either embodiment, after the rod seat 210, screw shank 2, and retainer collar 204 have been assembled and inserted into the bottom end 284 of the tulip head 208, the locking ring groove 234 of retainer collar 204 aligns and/or mates with retention groove 286 of tulip head 208 to form an annular channel about the bottom end 284. Once these components are assembled together as set forth above, the locking ring 206 may be inserted into the retention groove inlet 287 and into and around the channel formed from the locking ring groove 234 and retention groove 286. As set forth above, in some embodiments, the locking ring 206 is a wire. A sufficient length of wire is inserted into the retention groove inlet 287 and subsequently into and around the channel formed from the combination of the locking ring groove 234 and retention groove 286 in order to hold or lock the assembly to and within the tulip head 208. In some embodiments, the wire 206 is part of a spool of wire and thus when a sufficient length of wire is inserted into the channel formed from the locking ring groove 234 and retention groove 286, the wire may be severed from the remainder of the spool outside the tulip head 208, within the retention groove inlet 287 or within the retention groove 286 itself.

As set forth above, prior to insertion of the screw shank 2 and/or retainer collar 204 into the tulip head 208, rod seat 210 is inserted into tulip head 208 through lower opening 282. Rod seat 210 remains slideably and rotatably positioned in chamber 296 of tulip head 208, and screw shank 2 remains moveable with respect to tulip head 208 and rod seat 210. Movement of screw shank 2 in a poly-axial or uni-axial manner in relation to tulip head 208 and rod seat 210 depends on the configuration of spherical connector 22. In a poly-axial arrangement of spherical connector 22, where spherical connector 22 retains a curved profile around the entire periphery (approximately 360 degrees), the screw shank 2 may move in a poly-axial manner. In a uni-axial arrangement of spherical connector 22, where spherical connector 22 has flat angulation guides 26, the screw shank 2 may move in a uni-axial manner. However, in poly-axial configurations and uni-axial configurations without anti-rotation tabs 232a-h on the retainer collar 204, screw shank 2 may rotate about a longitudinal axis of the screw shank 2 relative to the tulip head 208.

As set forth above, when locking ring 206 is seated within retention groove 286 and locking ring groove 234, screw shank 2, retainer collar 204, and rod seat 210 are retained within lower opening 282 of tulip head 208. Rod seat 210 is supported by spherical connector 22 of screw shank 2, and spherical connector 22 is supported by spherical connector mating surfaces 236 of retainer collar 204. In an embodiment, retainer collar 204 is held around spherical connector 22 by locking ring 206 disposed in locking ring groove 234. Locking ring 206 is held by retention groove 286 of tulip head 208 and thus screw shank 2, retainer collar 204, and rod seat 210 are held in tulip head 208.

In some embodiments, pedicle screw 200 is assembled (as described above) prior to use in a surgical procedure. In some embodiments, it is envisioned that all or a portion of assembly may be completed in the operating theater. The bottom loading aspect of the assembly wherein the screw shank 2 is inserted into the tulip head 208 through lower opening 282 allows the same tulip head 208 to be used for screw shanks 2 of various thread diameter and/or pitch. A standard dimension of the spherical connector 22 is utilized for screw shanks 2 of different diameters and because the threaded portion of the screw shank 2 does not have to pass through tulip head 208 the geometry of tulip head 208 may be consistent.

The bottom loading configuration of pedicle screw 200 during the assembly process also allows for an overall lower profile tulip head 208.

In using the illustrated embodiment of pedicle screw 200, screw shank 2 of pedicle screw 200 is threaded into an appropriately prepared hole in a bone (not shown). The threaded portion of screw shank 2 is inserted into the hole, and an appropriate driving/screwing tool is used with driver receptacle 28 of screw shank 2 through hole 218 in rod seat 210, and screw shank 2 is threaded into the bone. When screw shank 2 has been threaded into the bone to the desired depth, tulip head 208 is positioned so that upper opening 281 forms a desired angle with screw shank 2 and U-shaped channel 292 is oriented in the desired direction. An elongated member such as a spinal rod, connector, or other orthopedic surgical implant is coupled with pedicle screw 200 by placing the elongated member in U-shaped channel 292 of tulip head 208 such that it contacts rod mating face 212 of rod seat 210. A compression member, such as a set screw or threaded plug, is threaded into internal threads 294 of tulip head 208 to secure the elongated member. As the compression member is tightened, elongated member is forced downward against rod seat 210, which pushes shank mating face 214 of rod seat 210 down onto spherical connector 22 of screw shank 2. Spherical connector 22 is thereby clamped between shank mating face 214 of rod seat 210 and spherical connector mating surface 36 of retainer collar 204. In this way, screw shank 2 is locked into the desired angular position with respect to elongated member and the remainder of pedicle screw 200.

Illustrative materials for use in one or more components of the pedicle screws shown and described herein include, but are not limited to, stainless steel, titanium, titanium alloys, and cobalt-chromium alloys such as, for example, cobalt-chromium-molybdenum alloys. It will be recognized that any sturdy biocompatible material may be used for one or more embodiments shown and described herein or any one or more of the subcomponents of these embodiments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made. It is therefore intended to cover in the appended claims all such changes and modifications.

The invention claimed is:

1. A pedicle screw comprising:
   a tulip head having an upper opening disposed in a top end of the tulip head, a lower opening disposed in a bottom end of the tulip head opposite the upper opening, and a pair of opposing arms, wherein:
      the upper and lower openings form a single cavity extending through the tulip head from the top end to the bottom end,
      the pair of opposing arms define a U-shaped channel transverse to the cavity, and
      the cavity has an interior wall, internal threads disposed within the interior wall and adjacent to the upper opening, and a stop disposed between the lower opening and the upper opening;
   a rod seat disposed within the cavity, the rod seat having:
      a rod mating face,
      a shank mating face opposite the rod mating face,
      a hole disposed through the rod mating face and shank mating face, and
      a pair of retention ledges, wherein the pair of retention ledges are engageable with the stop of the cavity of the tulip head to prevent the rod seat from moving into the upper opening of the tulip head, and wherein the pair of retention ledges are engageable with the pair of opposing arms of the tulip head to prevent rotation of the rod seat relative to the tulip head;
   a screw shank having a thread disposed along a length of the screw shank and a connector positioned at an upper end of the screw shank; and
   a retainer collar having a collar body, a pass through aperture disposed through the collar body, and a collar expansion split disposed within the collar body, wherein the retainer collar is disposed about the connector of the screw shank.

2. The pedicle screw of claim 1, wherein:
   the cavity of the tulip head has a retention groove disposed within the interior wall;
   the stop is disposed between the retention groove and the upper opening; and
   the retainer collar has a locking ring groove disposed within an outer surface of the collar body.

3. The pedicle screw of claim 2, further comprising a locking ring disposed within the retention groove and the locking ring groove.

4. The pedicle screw of claim 3, wherein the locking ring has a compression zone disposed therein such that when the compression zone is in its natural state it has an unloaded outer diameter ($D_{O1}$) and an unloaded inner diameter ($D_{I1}$), and wherein when the compression zone is reduced, the locking ring has a loaded outer diameter ($D_{O2}$) and a loaded inner diameter ($D_{I2}$).

5. The pedicle screw of claim 3, wherein the tulip head includes a retention groove inlet that is connected to the retention groove and extends to an exterior surface of the tulip head opposite the interior wall.

6. The pedicle screw of claim 5, wherein the locking ring is disposed in the retention groove inlet.

7. The pedicle screw of claim 6, wherein the locking ring is a wire fabricated from a material selected from a group consisting of metals, alloys, and composites.

8. The pedicle screw of claim 1, wherein each retention ledge of the pair of retention ledges comprises a first retention surface engageable with the stop of the cavity of the tulip head and a second retention surface engageable with a different opposing arm of the pair of opposing arms of the tulip head, the second retention surface of each retention ledge extends in a direction transverse to the first retention surface.

9. The pedicle screw of claim 1, wherein the retainer collar comprises an anti-rotation tab extending from the collar body; and
   wherein the cavity of the tulip head further includes an anti-rotation socket constructed to receive and engage the anti-rotation tab of the retainer collar.

10. A pedicle screw comprising:
    a tulip head having an upper opening disposed in a top end of the tulip head, a lower opening disposed in a bottom end of the tulip head opposite the upper opening, and a pair of opposing arms, wherein:
       the upper and lower openings form a single cavity extending through the tulip head from the top end to the bottom end,
       the pair of opposing arms define a U-shaped channel transverse to the cavity, and
       the cavity has an interior wall and internal threads, wherein the internal threads are disposed within the interior wall adjacent to the upper opening;
    a rod seat disposed within the cavity, the rod seat having:
       a rod mating face,
       a shank mating face opposite the rod mating face,
       a hole disposed through the rod mating face and shank mating face, and
       a pair of retention ledges engageable with the pair of opposing arms to prevent rotation of the rod seat relative to the tulip head;
    a screw shank having a thread disposed along a length of the screw shank and a connector positioned at an upper end of the screw shank;
    a retainer collar having a collar body, a pass through aperture disposed through the collar body, and a collar expansion split disposed within the collar body, wherein the retainer collar is disposed about the connector of the screw shank.

11. The pedicle screw of claim 10, wherein:
    the cavity of the tulip head has a retention groove disposed within the interior wall; and
    the retainer collar has a locking ring groove disposed within an outer surface of the collar body.

12. The pedicle screw of claim 11, further comprising a locking ring disposed within the retention groove and the locking ring groove.

13. The pedicle screw of claim 12, wherein the locking ring has a compression zone disposed therein such that when the compression zone is in its natural state it has an unloaded outer diameter ($D_{O1}$) and an unloaded inner diameter ($D_{I1}$), and wherein when the compression zone is reduced, the locking ring has a loaded outer diameter ($D_{O2}$) and a loaded inner diameter ($D_{I2}$).

14. The pedicle screw of claim 12, wherein the tulip head includes a retention groove inlet that is connected to the retention groove and extends to an exterior surface of the tulip head opposite the interior wall.

15. The pedicle screw of claim 14, wherein the locking ring is disposed in the retention groove inlet.

16. The pedicle screw of claim 15, wherein the locking ring is a wire fabricated from a material selected from a group consisting of metals, alloys, and composites.

17. The pedicle screw of claim 10, wherein the cavity of the tulip head comprises a stop disposed between the lower opening and the upper opening; and wherein the pair of retention ledges are engageable with the stop of the cavity of the tulip head to prevent the rod seat from moving into the upper opening of the tulip head.

18. The pedicle screw of claim 17, wherein each retention ledge of the pair of retention ledges comprises a first retention surface engageable with the stop of the cavity of the tulip head and a second retention surface engageable with a different opposing arm of the pair of opposing arms of the tulip head, the second retention surface of each retention ledge extends in a direction transverse to the first retention surface.

19. The pedicle screw of claim 10, wherein the retainer collar comprises a sharpened spherical connector mating edge, wherein the sharpened spherical connector mating edge depresses into the connector of the screw shank.

20. The pedicle screw of claim 10, wherein the retainer collar comprises an anti-rotation tab extending from the collar body; and wherein the cavity of the tulip head further includes an anti-rotation socket constructed to receive and engage the anti-rotation tab of the retainer collar.

* * * * *